United States Patent
Watson et al.

(10) Patent No.: US 6,723,327 B1
(45) Date of Patent: Apr. 20, 2004

(54) **METHODS AND COMPOUNDS FOR THE TREATMENT OF IMMUNOLOGICALLY-MEDIATED DISEASES USING *MYCOBACTERIUM VACCAE***

(75) Inventors: James D. Watson, Auckland (NZ); Paul L. J. Tan, Auckland (NZ); Ross Prestidge, Auckland (NZ); Nevin Abernethy, Auckland (NZ)

(73) Assignee: Genesis Research and Development Corporation, Parnell (NZ)

( * ) Notice: Subject to any disclaimer, the term of this patent is extended or adjusted under 35 U.S.C. 154(b) by 78 days.

(21) Appl. No.: 09/710,425

(22) Filed: Nov. 8, 2000

Related U.S. Application Data

(63) Continuation-in-part of application No. 09/449,013, filed on Nov. 24, 1999, now Pat. No. 6,350,457.
(60) Provisional application No. 60/137,112, filed on Jun. 2, 1999.

(30) Foreign Application Priority Data

Jun. 1, 2000 (NZ) .............................. PCT/NZ00/00085

(51) Int. Cl.$^7$ ..................... A61K 39/04; A61K 39/38; A61K 39/00; A61K 45/00; C12N 1/12
(52) U.S. Cl. ................ 424/248.1; 424/9.1; 424/9.2; 424/184.1; 424/234.1; 424/278.1; 424/282.1; 435/253.1
(58) Field of Search ................ 424/9.1, 9.2, 184.1, 424/234.1, 248.1, 278.1, 282.1; 435/253.1

(56) References Cited

U.S. PATENT DOCUMENTS

| | | | |
|---|---|---|---|
| 3,956,481 A | 5/1976 | Jolles et al. | .................. 424/92 |
| 4,036,953 A | 7/1977 | Adam et al. | .................. 424/92 |
| 4,503,048 A | 3/1985 | Cantrell | .................. 424/195 |
| 4,579,945 A | 4/1986 | Schwartzman et al. | ...... 336/127 |
| 4,716,038 A | 12/1987 | Stanford et al. | .............. 424/92 |
| 4,724,144 A | 2/1988 | Rook et al. | .................. 424/88 |
| 5,599,545 A | 2/1997 | Stanford et al. | ......... 424/282.1 |

FOREIGN PATENT DOCUMENTS

| | | | |
|---|---|---|---|
| EP | 0763361 | 3/1997 | .......... A61K/39/04 |
| WO | 9007935 | 7/1990 | .......... A61K/39/02 |
| WO | 9101751 | 2/1991 | .......... A61K/39/04 |
| WO | 9102542 | 3/1991 | .......... A61K/39/04 |
| WO | 9208484 | 5/1992 | .......... A61K/39/04 |
| WO | 9316727 | 9/1993 | .......... A61K/39/04 |
| WO | 9406466 | 3/1994 | .......... A61K/39/04 |
| WO | 9526742 | 10/1995 | .......... A61K/35/74 |
| WO | 9820900 | 5/1998 | .......... A61K/39/04 |

OTHER PUBLICATIONS

Hiu, I.J., "The adjuvant active fraction of delipidated mycobacteria," *Nature*, vol. 267, pp. 708–709 (Jun. 23, 1998).

Aoyama, B., "Lipopolysaccharide isolated from *Mycobacterium tuberculosis*strain," *Agric. Biol. Chem.*, vol. 51, No. 3, pp. 691–697 (1987)—Abstract.

Meyer, T.J., et al., "Biologically active components from mycobacterial cell walls. III. Production of experimental allergic encephalomyelitis in guinea–pigs," *Immunology*, vol. 28, No. 2, pp. 219–229 (Feb. 1975)—Abstract.

Melancon–Kaplan, Johanne et al., "Immunological significance of *Mycobacterium leprae* cell walls," *Proc. Nat'l. Acad. Sci.*, vol. 85, pp. 1917–1921 (Mar. 1998).

Hunter, Shirley Wu, et al., "Isolation and Characterization of the Highly Immunogenic Cell Wall–Associated Protein of *Mycobacterium leprae*," *The Journal of Immunology*, vol. 142, No. 8, pp. 2864–2872 (Apr. 15, 1989).

Azuma, Ichiro et al., "Fractionation of Mycobacterial Cell Wall," *Journal of Bacteriology*, vol. 96, pp. 1885–1887 (Nov. 1968).

Navalkar, Ram G., et al., "Antigenic Evaluation of *Mycobacterium vaccae* in Relation to *Mycobacterium leprae*," *International Journal of Lepros*, vol. 48, No. 4, pp. 388–396 (Dec., 1980).

Genesis Research & Development Corporation Limited, "Immunization with Heat–Killed *Mycobacterium vaccae* Stimulates CD8$^+$ Cytotoxic T Cells Specific for Macrophages Infected with *Mycobacterium tuberculosis*," *Infection and Immunity*, vol. 65, No. 11, pp. 4525–4530 (Nov. 1997).

White, R.G., et al., "The Influence of Components of M. Tuberculosis and other Mycobacteria upon Antibody Production to Ovalbumin," *Immunology*, vol. I, pp. 54–65 (1958).

White, R.G., "Characterization of Microbacterial Components of Adjuvant Mixtures," *International Symposium on Adjuvants of Immunity*, Utrecht 1966; *Symp. Series Immunobiol. Standard.*, vol. 6, pp. 49–58 (Karger, Barel/N.Y. 1967).

White, R.G., et al., "Correlation of Adjuvant Activity and Chemical Structure of Wax D Fractions of Mycobacteria," *Immunology*, vol. 7, No. 2, pp. 158–171 (1964).

*Primary Examiner*—Rodney P Swartz
(74) *Attorney, Agent, or Firm*—Ann W. Speckman; Janet Sleath

(57) ABSTRACT

Methods for the prevention and treatment of disorders, including disorders of the skin and respiratory system, such as infection with mycobacteria such as M. tuberculosis or *M. avium*, sarcoidosis, asthma, allergic rhinitis, allergic dermatitis and lung cancers are provided, such methods comprising administering a composition comprising at least one derivative of delipidated and deglycolipidated *M. vaccae* cells.

12 Claims, 12 Drawing Sheets

METHODS AND COMPOUNDS FOR THE TREATMENT OF IMMUNOLOGICALLY-MEDIATED DISEASES USING *MYCOBACTERIUM VACCAE*

CROSS-REFERENCE TO RELATED APPLICATIONS

This application is a continuation-in-part of U.S. application Ser. No. 09/449,013, filed Nov. 24, 1999, now U.S. Pat. No. 6,350,457, which claims priority to U.S. Provisional Patent Application No. 60/137,112, filed Jun. 2, 1999, and also claims the benefit of priority to PCT Application No. PCT/NZ00/00085, filed Jun. 1, 2000.

TECHNICAL FIELD

The present invention relates generally to methods for the treatment of immunologically-mediated disorders. In certain embodiments, the invention is related to the use of compositions comprising components prepared from *Mycobacterium vaccae*, Mycobacterium tuberculosis and *Mycobacterium smegmatis* for the treatment of immunologically-mediated disorders of the respiratory system, such as sarcoidosis, asthma and lung cancers, for treatment of allergic disorders such as atopic dermatitis and eczema, for treatment of diseases that benefit from the reduction of eosinophilia, for treatment and prevention of infectious diseases, such as infection with Mycobacterium tuberculosis or *Mycobacterium avium*, and for the treatment of atherosclerosis, hypercholesterolemia and other disorders that may be improved by modulating EL-10 production.

BACKGROUND OF THE INVENTION

Tuberculosis is a chronic, infectious disease that is caused by infection with Mycobacterium tuberculosis (M. tuberculosis). It is a major disease in developing countries, as well as an increasing problem in developed areas of the world, with about 8 million new cases and 3 million deaths each year. Although the infection may be asymptomatic for a considerable period of time, the disease is most commonly manifested as a chronic inflammation of the lungs, resulting in fever and respiratory symptoms. If left untreated, significant morbidity and death may result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistant mycobacteria.

Inhibiting the spread of tuberculosis requires effective vaccination and accurate, early diagnosis of the disease. Currently, vaccination with live bacteria is the most efficient method for inducing protective immunity. The most common mycobacterium employed for this purpose is Bacille Calmette-Guerin (BCG), an avirulent strain of *Mycobacterium bovis* (M. bovis). However, the safety and efficacy of BCG is a source of controversy and some countries, such as the United States, do not vaccinate the general public. Diagnosis of M. tuberculosis infection is commonly achieved using a skin test, which involves intradermal exposure to tuberculin PPD (protein-purified derivative). Antigen-specific T cell responses result in measurable induration at the injection site by 48–72 hours after injection, thereby indicating exposure to mycobacterial antigens. Sensitivity and specificity have, however, been a problem with this test, and individuals vaccinated with BCG cannot be distinguished from infected individuals.

A less well-known mycobacterium that has been used for immunotherapy for tuberculosis, and also leprosy, is *Mycobacterium vaccae* (M. vaccae), which is non-pathogenic in humans. However, there is less information on the efficacy of M. vaccae compared with BCG, and it has not been used widely to vaccinate the general public. M. bovis BCG and M. vaccae are believed to contain antigenic compounds that are recognized by the immune system of individuals exposed to infection with M. tuberculosis.

Several patents and other publications disclose treatment of various conditions by administering mycobacteria, including M. vaccae, or certain mycobacterial fractions. U.S. Pat. No. 4,716,038 discloses diagnosis of, vaccination against, and treatment of autoimmune diseases of various types, including arthritic diseases, by administering mycobacteria, including M. vaccae. U.S. Pat. No. 4,724,144 discloses an immunotherapeutic agent comprising antigenic material derived from M. vaccae for treatment of mycobacterial diseases, especially tuberculosis and leprosy, and as an adjuvant to chemotherapy. International Patent Publication WO 91/01751 discloses the use of antigenic and/or immunoregulatory material from M. vaccae as an immunoprophylactic to delay and/or prevent the onset of AIDS. International Patent Publication WO 94/06466 discloses the use of antigenic and/or immunoregulatory material derived from M. vaccae for therapy of HIV infection, with or without AIDS and with or without associated tuberculosis.

U.S. Pat. No. 5,599,545 discloses the use of mycobacteria, especially whole, inactivated M. vaccae, as an adjuvant for administration with antigens that are not endogenous to M. vaccae. This publication theorizes that the beneficial effect as an adjuvant may be due to heat shock protein 65 (hsp65). International Patent Publication WO 92/08484 discloses the use of antigenic and/or immunoregulatory material derived from M. vaccae for the treatment of uveitis. International Patent Publication WO 93/16727 discloses the use of antigenic and/or immunoregulatory material derived from M. vaccae for the treatment of mental diseases associated with an autoimmune reaction initiated by an infection. International Patent Publication WO 95/26742 discloses the use of antigenic and/or immunoregulatory material derived from M. vaccae for delaying or preventing the growth or spread of tumors. International Patent Publication WO 91/02542 discloses the use of autoclaved M. vaccae in the treatment of chronic inflammatory disorders in which a patient demonstrates an abnormally high release of IL-6 and/or TNF or in which the patient's IgG shows an abnormally high proportion of agalactosyl IgG. Among the disorders mentioned in this publication are psoriasis, rheumatoid arthritis, mycobacterial disease, Crohn's disease, primary biliary cirrhosis, sarcoidosis, ulcerative colitis, systemic lupus erythematosus, multiple sclerosis, Guillain-Barre syndrome, primary diabetes mellitus, and some aspects of graft rejection.

M. vaccae is apparently unique among known mycobacterial species in that heat-killed preparations retain vaccine and immunotherapeutic properties. For example, M. bovis BCG vaccines, used for vaccination against tuberculosis, employ live strains. Heat-killed M. bovis BCG and M. tuberculosis have no protective properties when employed in vaccines. A number of compounds have been isolated from a range of mycobacterial species that have adjuvant properties. The effect of such adjuvants is essentially to stimulate a particular immune response mechanism against an antigen from another species.

There are two general classes of compounds that have been isolated from mycobacterial species that exhibit adjuvant properties. The first are water-soluble wax D fractions (White et al., *Immunology* 1:54, 1958; U.S. Pat. No. 4,036, 953). The second are muramyl dipeptide-based substances (N-acetyl glucosamine and N-glycolymuramic acid in approximately equimolar amounts) as described in U.S. Pat. No. 3,956,481 and 4,036,953. These compounds differ from the delipidated and deglycolipidated *M. vaccae* (DD-*M. vaccae*) of the present invention in the following aspects of their composition:

1. They are water-soluble agents, whereas DD-*M. vaccae* is insoluble in aqueous solutions.
2. They consist of a range of small oligomers of the mycobacterial cell wall unit, either extracted from bacteria by various solvents, or digested from the cell wall by an enzyme. In contrast, DD-*M. vaccae* comprises processed mycobacterial cells.
3. All protein has been removed from their preparations by digestion with proteolytic enzymes. The only constituents of their preparations are the components of the cell wall peptidoglycan structure, namely alanine, glutamic acid, diaminopimelic acid, N-acetyl glucosamine, and N-glycolylmuramic acid. In contrast, DD-*M. vaccae* contains 50% w/w protein, comprising a number of distinct protein species.

Sarcoidosis is a disease of unknown cause characterized by granulomatous inflammation affecting many organs of the body and especially the lungs, lymph nodes and liver. Sarcoid granulomata are composed of mononuclear phagocytes, with epithelioid and giant cells in their center, and T lymphocytes. CD4 T lymphocytes are closely associated with the epithelloid cells while both CD4 and CD8 T lymphocytes accumulate at the periphery. The characteristic immunological abnormalities in sarcoidosis include peripheral blood and bronchoalveolar lavage hyper-globulinaemia and depression of 'delayed type' hypersensitivity reactions in the skin to tuberculin and other similar antigens, such as Candida and mumps. Peripheral blood lymphocyte numbers are reduced and CD4: CD8 ratios in peripheral blood are depressed to approximately 1–1.5:1. These are not manifestations of a generalized immune defect, but rather the consequence of heightened immunological activity which is 'compartmentalized' to sites of disease activity. In patients with pulmonary sarcoidosis, the total number of cells recovered by bronchoalveolar lavage is increased five- to ten-fold and the proportion of lymphocytes increased from the normal of less than 10–14% to between 15%, and 50%. More than 90% of the lymphocytes recovered are T lymphocytes and the CD4:CD8 ratio has been reported to be increased from the value of 1.8:1 in normal controls to 10.5:1. The T lymphocytes are predominantly of the Th1 class, producing INF-γ and IL-2 cytokines, rather than of the Th2 class. Following treatment, the increase in Th1 lymphocytes in sarcoid lungs is corrected.

Sarcoidosis involves the lungs in nearly all cases. Even when lesions are predominantly seen in other organs, subclinical lung involvement is usually present. While some cases of sarcoidosis resolve spontaneously, approximately 50% of patients have at least a mild degree of permanent organ dysfunction. In severe cases, lung fibrosis develops and progresses to pulmonary failure requiring lung transplantation. The mainstay of treatment for sarcoidosis is corticosteroids. Patients initially responding to corticosteroids often relapse and require treatment with other immunosuppressive drugs such as methotrexate or cyclosporine.

Asthma is a common disease, with a high prevalence in the developed world. Asthma is characterized by increased responsiveness of the tracheobronchial tree to a variety of stimuli, the primary physiological disturbance being reversible airflow limitation, which may be spontaneous or drug-related, and the pathological hallmark being inflammation of the airways. Clinically, asthma can be subdivided into extrinsic and intrinsic variants.

Extrinsic asthma has an identifiable precipitant, and can be thought of as being atopic, occupational and drug-induced. Atopic asthma is associated with the enhancement of a Th2-type of immune response with the production of specific immunoglobulin E (IgE), positive skin tests to common aeroallergens and/or atopic symptoms. It can be divided further into seasonal and perennial forms according to the seasonal timing of symptoms. The airflow obstruction in extrinsic asthma is due to nonspecific bronchial hyper-esponsiveness caused by inflammation of the airways. This inflammation is mediated by chemicals released by a variety of inflammatory cells including mast cells, eosinophils and lymphocytes. The actions of these mediators result in vascular permeability, mucus secretion and bronchial smooth muscle constriction. In atopic asthma, the immune response producing airway inflammation is brought about by the Th2 class of T cells which secrete IL-4, IL-5 and IL-10. It has been shown that lymphocytes from the lungs of atopic asthmatics:produce IL-4 and IL-5 when activated. Both IL-4 and IL-5 are cytokines of the Th2 class and are required for the production of IgE and involvement of eosinophils in asthma. Occupational asthma may be related to the development of IgE to a protein hapten, such as acid anhydrides in plastic workers and plicatic acid in some western red cedar-induced asthma, or to non-IgE related mechanisms, such as that seen in toluene dusocyanate-induced asthma. Drug-induced asthma can be seen after the administration of aspirin or other non-steroidal anti-inflammatory drugs, most often in a certain subset of patients who may display other features such as nasal polyposis and sinusitis. Intrinsic or cryptogenic asthma is reported to develop after upper respiratory tract infections, but can arise de novo in middle-aged or older people, in whom it is more difficult to treat than extrinsic asthma.

Asthma is ideally prevented by the avoidance of triggering allergens but this is not always possible nor are triggering allergens always easily identified. The medical therapy of asthma is based on the use of corticosteroids and bronchodilator drugs to reduce inflammation and reverse airway obstruction. In chronic asthma, treatment with corticosteroids leads to unacceptable adverse side effects.

Another disorder with a similar immune abnormality to asthma is allergic rhinitis. Allergic rhinitis is a common disorder and is estimated to affect at least 10% of the population. Allergic rhinitis may be seasonal (hay fever) caused by allergy to pollen. Non-seasonal or perennial rhinitis is caused by allergy to antigens such as those from house dust mite or animal dander.

The abnormal immune response in allergic rhinitis is characterized by the excess production of IgE antibodies specific against the allergen. The inflammatory response occurs in the nasal mucosa rather than further down the airways as in asthma. Like asthma, local eosinophilia in the affected tissues is a major feature of allergic rhinitis. As a result of this inflammation, patients develop sneezing, nasal discharge and congestion. In more severe cases, the inflammation extends to the eyes (conjunctivitis), palate and the external ear. While it is not life threatening, allergic rhinitis may be very disabling, prevent normal activities, and interfere with a person's ability to work. Current treatment involves the use of antihistamines, nasal decongestants and, as for asthma, sodium cromoglycate and corticosteroids.

Atopic dermatitis, also known as atopic eczema, is a chronic and recurrent pruritic-inflammatory skin disease which usually occurs in families with an hereditary predisposition for various allergic disorders, such as allergic rhinitis and asthma. Atopic dermatitis is increasing in prevalence with up to 15% of the population having had atopic dermatitis during childhood. The main symptoms are dry skin and dermatitis (eczema) localized mainly in the face, neck and on the flexor sides and folds of the extremities, accompanied by severe itching. It typically starts within the first five years of life. In many patients this skin disease disappears during childhood but the symptoms can continue into adult life. Furthermore, 50% of patients develop asthma and approximately 75% develop allergic rhinitis. It is one of the commonest forms of dermatitis worldwide.

Allergens play an important role in atopic dermatitis. Approximately 80% of patients have IgE antibodies to a variety of food and inhaled allergens, with the majority of patients with severe atopic dermatitis having elevated levels of serum IgE, particularly if they also have other forms of atopic disease. In addition, circulating levels of blood eosinophils are often elevated. In atopic dermatitis, the dermis of skin lesions is infiltrated with macrophages, T cells and eosinophils, and in chronic lesions there are increased numbers of mast cells. Acute lesions have significantly more cells expressing the cytokines IL-4, IL-5 and IL-13, indicating preferential accumulation of the Th2 class of T cells. In addition, circulating T cells in atopic dermatitis patients produce more IL-4 and IL-5, compared to normal individuals. The Th2 cytokines have an important role in initiating the allergic response. IL-4 is responsible for switching antibody production to the IgE isotype, the development of Th2 cells and induction of adhesion molecules on endothelial cells that recruit eosinophils. IL-5 is important for the development and differentiation of eosinophils.

Unlike Th2 cells, Th1 cells produce IFNγ and IL-2. Th1 cells have been identified in chronic atopic skin lesions. As IL-2 is important for T cell growth and has the effect of causing abnormal dermal thickening, Th1 cells may also contribute to the pathology in atopic dermatitis. In mice, atopic dermatitis-like lesions can be caused by repeated epicutaneous sensitization with ovalbumin. The draining lymph node T cells from these mice secrete IL-4 but not IFNγ in response to in vitro stimulation with ovalbumin.

Allergic contact dermatitis is a common non-infectious inflammatory disorder of the skin. In contact dermatitis, immunological reactions cannot develop until the body has become sensitised to a particular antigen. Subsequent exposure of the skin to the antigen and the recognition of these antigens by T cells result in the release of various cytokines, proliferation and recruitment of T cells and finally in dermatitis (eczema).

Only a small proportion of the T cells in a lesion of allergic contact dermatitis are specific for the relevant antigen. Activated T cells probably migrate to the sites of inflammation regardless of antigen-specificity. Delayed-type hypersensitivity can only be transferred by T cells (CD4+ cells) sharing the MHC class II antigens. The 'response' to contact allergens can be transferred by T cells sharing either MHC class I (CD8+ cells) or class II (CD4+ cells) molecules (Sunday, el al., *J. Immunol.* 125:1601–1605, 1980). Keratinocytes can produce interleukin-1 which can facilitate the antigen presentation to T cells. The expression of the surface antigen intercellular adhesion molecule-1 (ICAM-1) is induced both on keratinocytes and endothelium by the cytokines tumor necrosis factor (TNF) and interferon-gamma (IFN-γ).

If the causes can be identified, removal alone will cure allergic contact dermatitis. During active inflammation, topical corticosteroids are useful. An inhibitory effect of cyclosporin has been observed in delayed-type hypersensitivity on the pro-inflammatory function(s) of primed T cells in vitro (Shidani, et al., *Eur. J. Immunol.* 14:314–318, 1984). The inhibitory effect of cyclosporin on the early phase of T cell activation in mice has also been reported (Milon, et al., *Ann. Immunol.* (*Inst. Pasteur*) 135d:237–245, 1984).

Lung cancer is the leading cause of death from cancer. The incidence of lung cancer continues to rise and the World Health Organization estimates that by 2000 AD there will be 2 million new cases annually. Lung cancers may be broadly classified into two categories: small cell lung cancer (SCLC) which represents 20–25% of all lung cancers, and non-small cell lung cancer (NSCLC) which accounts for the remaining 75%. The majority of SCLC is caused by tobacco smoke. SCLC tends to spread early and 90% of patients present at diagnosis with involvement of the mediastinal lymph nodes in the chest. SCLC is treated by chemotherapy, or a combination of chemotherapy and radiotherapy. Complete response rates vary from 10% to 50%. For the rare patient without lymph node involvement, surgery followed by chemotherapy may result in cure rates exceeding 60%. The prognosis for NSCLC is more dismal, as most patients have advanced disease by the time of diagnosis. Surgical removal of the tumor is possible in a very small number of patients and the five year survival rate for NSCLC is only 5–10%.

The factors leading to the development of lung cancer are complex and multiple. Environmental and genetic factors interact and cause sequential and incremental abnormalities that lead to uncontrolled cell proliferation, invasion of adjacent tissues and spread to distant sites. Both cell-mediated and humoral immunity have been shown to be impaired in patients with lung cancer. Radiotherapy and chemotherapy further impair the immune function of patients. Attempts have been made to immunize patients with inactivated tumor cells or tumor antigens to enhance host anti-tumor response. Bacille Calmette-Guerin (BCG) has been administered into the chest cavity following lung cancer surgery to augment non-specific immunity. Attempts have been made to enhance anti-tumor immunity by giving patients lymphocytes treated ex vivo with interleukin-2 (IL-2). These lymphokine-activated lymphocytes acquire the ability to kill tumor cells. Current immunotherapies for lung cancer are still at a developmental stage and their efficacies have yet to be established for the standard management of lung cancer.

Atherosclerosis is a chronic inflammatory disease of the arterial wall that is characterized by accumulation of lipids, macrophages, T lymphocytes, smooth muscle cells and extracellular matrix. Anti-inflammatory cytokines are produced during the inflammatory reaction and are believed to modulate the inflammatory process. Interleukin-10 (IL-10) is secreted by Th2 lymphocytes and by macrophages, and is known to have anti-inflammatory properties. Mallat et al. recently reported studies in which IL-10 was shown to have a protective effect in the formation and stability of atherosclerotic lesions in mice (*Circ. Res.* 85:e17–24, 1999). These studies suggest that agents that increase IL-10 production may be employed to modulate the extent and/or severity of atherosclerosis.

Other disorders in which administration of IL-10 has been shown to beneficial include hypercholesterolemia (see, U.S.

Pat. No. 5,945,097); bacterial infections, including infection with gram-negative and/or gram-positive bacteria (see U.S. Pat. Nos. 5,837,293 and 5,837,232); and insulin-dependent diabetes mellitus (see, U.S. Pat. No. 5,827,513). In addition, U.S. Pat. No. 5,871,725 discloses a method of treating cancer by administering to a patient peripheral blood mononuclear cells (PBMC) that have been activated with IL-10.

SUMMARY OF THE INVENTION

Briefly stated, the present invention provides compositions and methods for the prevention and treatment of immunologically-mediated disorders, including disorders of the respiratory system (such as infection with mycobacteria such as M. tuberculosis or *Mycobacterium avium* (*M. avium*), sarcoidosis, asthma, allergic rhinitis and lung cancers), allergic disorders such as atopic dermatitis and eczema, diseases that benefit from the reduction of eosinophilia, and disorders that may be improved by modulating IL-10 production (such as atherosclerosis, hypercholesterolemia, cancer, bacterial infections and insulin-dependent diabetes mellitus).

In a first aspect, compositions comprising delipidated and deglycolipidated mycobacterial cells are provided. In specific embodiments, the delipidated and deglycolipidated cells are prepared from *M. vaccae*, M. tuberculosis and/or *M. smegmatis*.

In a second aspect, the present invention provides compositions comprising a derivative of delipidated and deglycolipidated mycobacterial cells, the derivative of delipidated and deglycolipidated mycobacterial cells being selected from the group consisting of: delipidated and deglycolipidated mycobacterial cells that have been treated by alkaline hydrolysis; delipidated and deglycolipidated mycobacterial cells that have been treated by acid hydrolysis; delipidated and deglycolipidated mycobacterial cells that have been treated with periodic acid; delipidated and deglycolipidated mycobacterial cells that have been treated with Proteinase K; and delipidated and deglycolipidated mycobacterial cells that have been treated by anhydrous hydrofluoric acid hydrolysis. The derivatives of delipidated and deglycolipidated *M. vaccae* preferably contain galactose in an amount less than 9.7% of total carbohydrate, more preferably less than 5% of total carbohydrate, and most preferably less than 3.5% total carbohydrate. In certain embodiments, the derivatives of delipidated and deglycolipidated *M. vaccae* contain glucosamine in an amount greater than 3.7% of total carbohydrate, preferably greater than 5% total carbohydrate and more preferably greater than 7.5% total carbohydrate.

In further aspects of this invention, methods are provided for the treatment of a disorder in a patient, including disorders of the respiratory system and skin, such methods comprising administering to the patient a composition of the present invention. In certain embodiments, the disorder is selected from the group consisting of mycobacterial infections, asthma, sarcoidosis, allergic rhinitis, atopic dermatitis and lung cancers. In one embodiment, the compositions are administered to the airways leading to or located within the lungs, preferably by inhalation through the nose or mouth, and are preferably administered in aerosol forms. The compositions may also, or alternatively, be administered by intradermal, transdermal or subcutaneous routes.

In another aspect, the present invention provides methods for the treatment of a disorder of the respiratory system and skin in a patient by the administration of a composition of the present invention, wherein the disorder is characterized by the presence of eosinophilia in the tissues of the respiratory system. Examples of such diseases include asthma and allergic rhinitis. In a related aspect, the present invention provides methods for the reduction of eosinophilia in a patient, such methods comprising administering at least one of the compositions disclosed herein. The reduction in eosinophilia will vary between about 20% and about 80%, preferably between 80% and 100%, and most preferably between 90% and 100%. The percentage of reduction in lung eosinophilia can be determined by measuring the number of eosinophils in bronchoalveolar lavage fluid before and after treatment as described below.

In yet a further aspect, methods for enhancing the production of IL10 are provided, such methods comprising administering a composition of the present invention. As discussed above, it has recently been shown that IL-10 plays a protective role in the formation and stability of atherosclerotic lesions. IL-10 has also been shown to be effective in the treatment of hypercholesterolemia, cancer, bacterial infections, and insulin-dependent diabetes mellitus. The inventive compositions may thus be usefully employed in the treatment of such disorders.

In another aspect, the present invention provides an immunoregulatory composition for modulating a Th2-mediated immune response to a specific antigen. The composition comprises delipidated and deglycolipidated *M. vaccae* cells that have been treated by acid hydrolysis (referred to herein as Avac). In one embodiment, the composition also comprises a specific antigen.

In a further aspect, the present invention provides a method for modulating a Th2-mediated immune response to a specific antigen in a patient, comprising administering a composition of the present invention.

In still another aspect, the present invention provides a method for the treatment of a disorder in a patient, comprising modulating the amount of an interleukin molecule involved in an antigen-specific Th2-mediated immune response by administering a composition of the present invention to the patient. Such disorders are characterized by one or more of the following: an hypersensitivity immune reaction; a pathogenic immune response caused by excessive Th2 activation; and a disorder caused by the suppression of an IFN-gamma-mediated immune function.

In a further aspect, the present invention provides for preventing or reducing the severity of an immune response to a specific antigen in a patient, comprising administering to the patient a specific antigen and a composition of the present invention. In a preferred embodiment, the specific antigen is an allergen. Preferably, at least one component of the composition comprises delipidated and deglycolipidated mycobacterial cells that have been treated by acid hydrolysis, and preferably, the composition is administered at the time of sensitization or exposure of the patient to a specific antigen.

The present invention further provides methods for the activation of $\alpha\beta$ T cells, $\gamma\delta$ T cells or NK cells, and thereby repairing epithelium in a patient, such methods comprising administering to the patient a composition of the present invention.

These and other aspects of the present invention will become apparent upon reference to the following detailed description and attached drawings. All references disclosed herein are hereby incorporated by reference in their entirety as if each was incorporated individually.

DETAILED DESCRIPTION OF THE INVENTION

Figure 1:
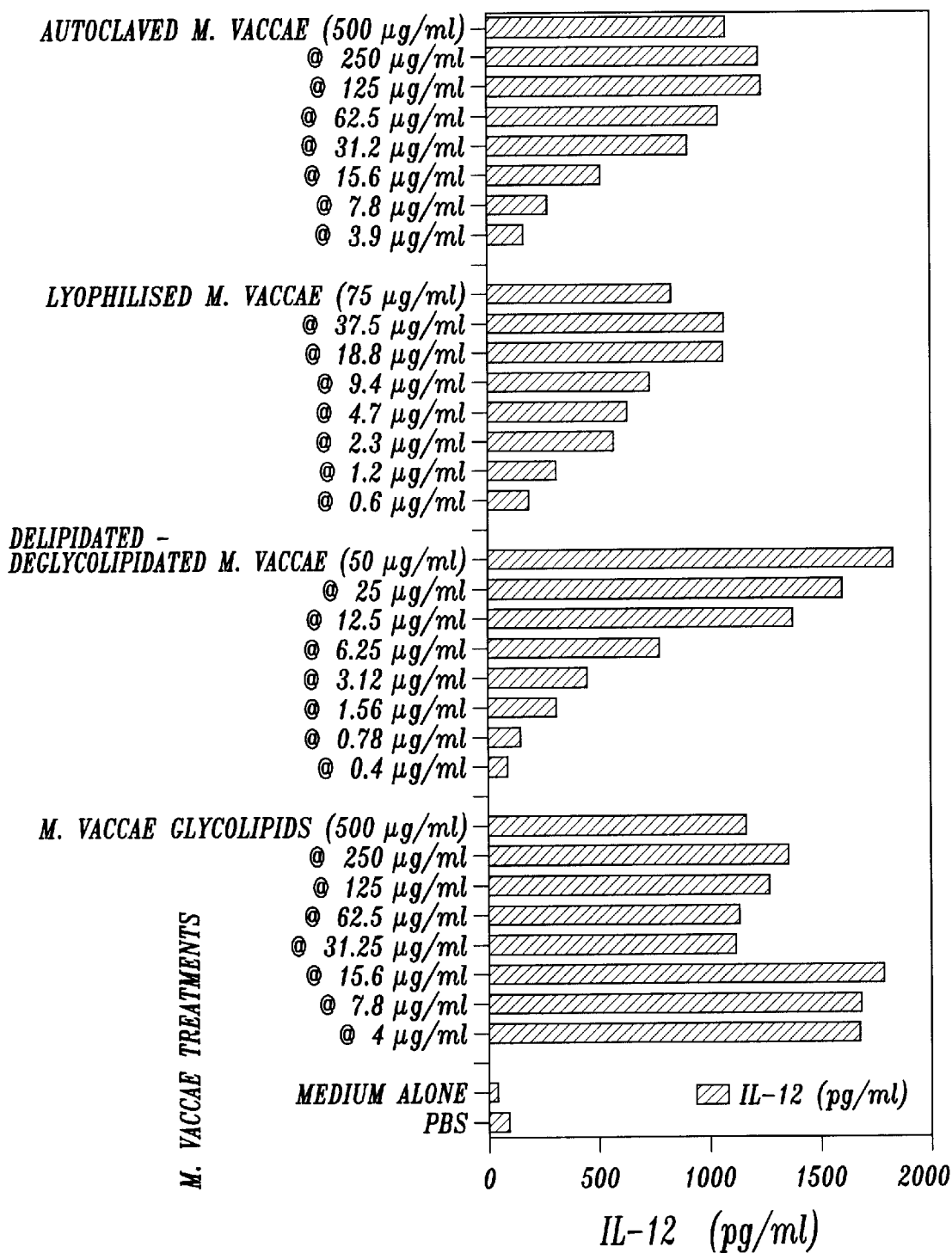
FIG. 1 illustrates the induction of IL-12 by autoclaved *M. vaccae*, lyophilized *M. vaccae*, delipidated and deglycolipidated *M. vaccae*, and *M. vaccae* glycolipids.

As noted above, the present invention is generally directed to compositions and methods for the treatment of immunologically-mediated disorders. In certain specific embodiments, such disorders are selected from the group consisting of disorders of the respiratory system, allergic disorders, other disorders involving Th2-mediated responses to specific antigens and disorders in which administration of IL-10 and/or stimulation of IL-10 production are beneficial. Examples of respiratory system disorders include mycobacterial infection, asthma, sarcoidosis, allergic rhinitis and lung cancer. Examples of disorders in which administration and/or increased production of IL-10 are believed to be beneficial include atherosclerosis, hypercholesterolemia, cancer, bacterial infections, and insulin-dependent diabetes mellitus. Examples of allergic skin disorders include atopic dermatitis and eczema. Examples of disorders involving Th2-mediated responses to specific antigens include hypersensitivity reactions, pathogenic immune responses caused by excessive Th2 activation (e.g., fibrotic responses to schistosome ova) and disorders caused by an interference with IFN-gamma-mediated immune functions.

Certain pathogens, such as M. tuberculosis, as well as certain cancers, are effectively contained by an immune attack directed by CD4+ T cells, known as cell-mediated immunity. Other pathogens, such as poliovirus, also require antibodies, produced by B cells, for containment. These different classes of immune attack (T cell or B cell) are controlled by different subpopulations of CD4+ T cells, commonly referred to as Th1 and Th2 cells.

The two types of Th cell subsets have been well characterized in a murine model and are defined by the cytokines they release upon activation. The Th1 subset secretes IL-2, INF-γ and tumor necrosis factor, and mediates macrophage activation and delayed-type hypersensitivity response. The Th2 subset releases IL-4, IL-5, IL-6 and IL-10, which stimulate B cell activation. The Th1 and Th2 subsets are mutually inhibiting, so that IL-4 inhibits Th1-type responses, and INF-γ inhibits Th2-type responses. Similar Th1 and Th2 subsets have been found in humans, with release of the identical cytokines observed in the murine model. Amplification of Th1-type immune responses is central to a reversal of disease state in many disorders, including disorders of the respiratory system such as tuberculosis, sarcoidosis, asthma, allergic rhinitis and lung cancers. IL-12 has been shown to up-regulate Th1 responses, while IL-10 has been shown to down-regulate Th2 responses. Zuany-Amorim et al. have shown that IL-10 regulates leukocyte infiltration into the airways of antigen-challenged mice, indicating that IL-10 plays an important role in regulating allergic inflammatory processes in the lung. (*J. Clin. Ivest.* 95:2644–2651, 1995). Studies by Borish et al. have found that bronchoalveolar fluid from asthmatic patients contains reduced levels of IL-10 compared to that from normal donors (*J. Allergy Clin. Immunol.* 97:1288–96, 1996).

Figure 21:
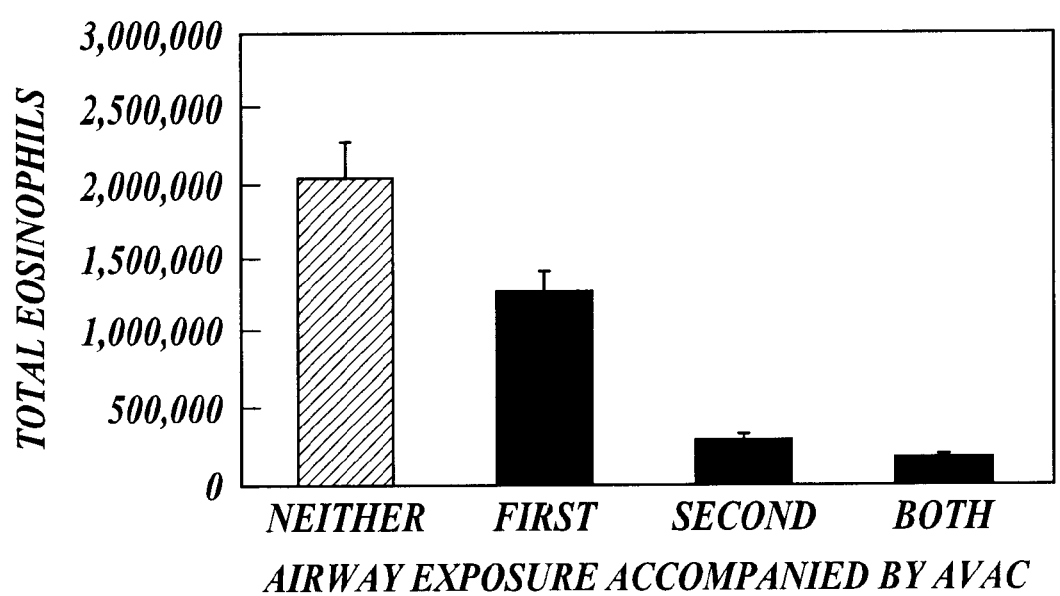
FIG. 21 illustrates the effect of DD-M. vaccae-acid on the development of allergen-induced airway eosinophilia when the DD-M. vaccae-acid is coadministered at the time of the first or second or both challenges to OVA.

In connection with the present invention, it has been discovered that delipidated and deglycolipidated *M. vaccae* cells prepared by acid hydrolysis (Avac) have pronounced immunoregulatory effects on both Th2 and Th1 cells. Thus, for example, Avac suppresses development of allergic airway disease, as determined by the degree of airway tissue eosinophilia, by greater than 90% when coadministered with specific antigen during priming (FIG. 18) or during challenge (FIG. 21). When coadministered with specific antigen during challenge, Avac reduces the amount of Th2 interleukin IL-4 and 5, increases the amount of IL10 (a regulatory or anti-inflammatory interleukin) and increases the content of the Th1 cytokine INF-γ in airway tissue. OVA-stimulated proliferation was completely inhibited in cultured mediastinal lymph node cells from Avac-treated, OVA-challenged mice, but was not inhibited in mice that were challenged with OVA in the absence of Avac (data not shown). Both cultures proliferated in response to ConA (data not shown).

While not wishing to be bound by theory, these results taken together suggest that Avac may act, at least in part, to modulate the development and differentiation of Th2 cells, and the function of both Th2 and Th1 cells.

In one aspect, methods are provided for the treatment of respiratory and/or lung disorders, comprising administering delipidated and deglycolipidated mycobacterial cells, preferably delipidated and deglycolipidated M. tuberculosis cells and/or delipidated and deglycolipidated *M. smegmatis* cells. In a related aspect, the present invention provides methods for the immunotherapy of respiratory and/or lung disorders, including tuberculosis, sarcoidosis, asthma, allergic rhinitis and lung cancers, in a patient by administration of a composition that comprises at least one derivative of delipidated and deglycolipidated mycobacterial cells. In certain specific embodiments, such methods comprise administering at least one derivative of DD-*M. vaccae*. As detailed below, the inventors have demonstrated the efficacy of such compositions in the treatment of asthma employing a mouse model. These compositions are believed to be effective in the treatment of diseases such as asthma due to their ability to suppress asthma-inducing Th2 immune responses. In one embodiment, the compositions are delivered directly to the mucosal surfaces of airways leading to and/or within the lungs. However, the compositions may also, or alternatively, be administered via intradermal or subcutaneous routes.

As used herein the term "respiratory system" refers to the lungs, nasal passageways, trachea and bronchial passageways.

As used herein the term "airways leading to or located in the lung" includes the nasal passageways, mouth, tonsil tissue, trachea and bronchial passageways.

As used herein, a "patient" refers to any warm-blooded animal, preferably a human. Such a patient may be afflicted with disease or may be free of detectable disease. In other words, the inventive methods may be employed to induce protective immunity for the prevention or treatment of disease.

As used herein the term "inactivated *M. vaccae*" refers to *M. vaccae* cells that have either been killed by means of heat, as detailed below in Example 1, or by exposure to radiation, such as $^{60}$Cobalt at a dose of 2.5 megarads. As used herein, the term "modified *M. vaccae*" includes delipidated *M. vaccae* cells, deglycolipidated *M. vaccae* cells, *M. vaccae* cells that have been both delipidated and deglycolipidated (DD-*M. vaccae*), and derivatives of delipidated and deglycolipidated *M. vaccae* cells. DD-*M. vaccae* may be prepared as described below in Example 1, with the preparation of derivatives of DD-*M. vaccae* being detailed below in Example 2. The preparation of delipidated and deglycolipidated M. tuberculosis (DD-M. tuberculosis) and *M. smegmatis* (DD-*M. smegmatis*) is described in Example 10 below. Derivatives of DD-M. tuberculosis and DD-*M. smegmatis*, such as acid-treated, alkali-treated, periodate-treated, proteinase K-treated, and/or hydrofluoric acid-treated derivatives, may be prepared using the procedures disclosed herein for the preparation of derivatives of DD-*M. vaccae*.

The derivatives of DD-*M. vaccae* preferably contain galactose in an amount less than 9.7% of total carbohydrate, more preferably less than 5% of total carbohydrate, and most preferably less than 3.5% total carbohydrate. In certain embodiments, the derivatives of DD-*M. vaccae* preferably contain glucosamine in an amount greater than 3.7% of total carbohydrate, more preferably greater than 5% total carbohydrate, and most preferably greater than 7.5% total carbohydrate. Derivatives prepared by treatment of DD-*M. vaccae* with alkali, such as DD-*M. vaccae*-KOH (also known as Kvac), have a reduced number of ester bonds linking mycolic acids to the arabinogalactan of the cell wall compared to DD-*M. vaccae*, and are thus depleted of mycolic acids. Derivatives prepared by treatment with acid, such as DD-*M. vaccae*-acid (also referred to as Avac), have a reduced number of phosphodiester bonds attaching arabinogalactan sidechains to the peptidoglycan of the cell wall, and are therefore depleted of arabinogalactan. In addition, such derivatives are depleted of DNA. Derivatives prepared by treatment of DD-*M. vaccae* with periodate, such as DD-*M. vaccae*-periodate (also known as Ivac), have a reduced number of cis-diol-containing sugar residues compared to DD-*M. vaccae* and are depleted of arabinogalactan. Derivatives prepared by treatment of DD-*M. vaccae* with Proteinase K (such as the derivative referred to as Evac) are depleted of proteins and peptides. Derivatives prepared by treatment with hydrofluoric acid, such as DD-*M. vaccae*-KOH treated with hydrofluoric acid (referred to as Hvac), are depleted of glycosidic bonds.

In general, the inventive compositions may be administered by injection (e.g., intradermal, intramuscular, intravenous or subcutaneous), intranasally (e.g., by aspiration), orally or epicutaneously (applied topically onto skin). In one embodiment, the compositions of the present invention are in a form suitable for delivery to the mucosal surfaces of the airways leading to or within the lungs. For example, the composition may be suspended in a liquid formulation for delivery to a patient in an aerosol form or by means of a nebulizer device similar to those currently employed in the treatment of asthma.

For use in therapeutic methods, the inventive compositions may additionally contain a physiologically acceptable carrier and/or an immunostimulant that elicits and/or stimulates an immune response, such as an adjuvant or a liposome, into which the polypeptide is incorporated. While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the compositions of this invention to enhance the immune response. Most adjuvants contain a substance designed a to protect the antigen from rapid catabolism, such as aluminum hydroxide or mineral oil, and a non-specific stimulator of immune responses, such as lipid A, Bordetella pertussis, M. tuberculosis, or, as discussed below, M. vaccae. Suitable adjuvants are commercially available as, for example, Freund's Incomplete Adjuvant and Freund's Complete Adjuvant (Difco Laboratories, Detroit, Mich.), and Merck Adjuvant 65 (Merck and Company, Inc., Rahway, N.J.). Other suitable adjuvants include alum, biodegradable microspheres, mnonophosphoryl lipid A and Quil A.

The preferred frequency of administration and effective dosage will vary from one individual to another. For both DD-M. vaccae and derivatives of DD-M. vaccae, the amount present in a dose preferably ranges from about 10 μg to about 1000 μg, more preferably from about 10 μg to about 100 μg. The number of doses may range from 1 to about 10 administered over a period of up to 12 months.

The word "about," when used in this application with reference to the amount of active component in a dose, contemplates a variance of up to 5% from the stated amount. The word "about," when used with reference to a percentage reduction of eosinophils, contemplates a variance of up to 10% from the stated percentage.

The following examples are offered by way of illustration and are not limiting.

EXAMPLE 1

Preparation of Delipidated and Deglycolipidated M. vaccae Cells (DD-M. vaccae)

This example illustrates the processing of different constituents of M. vaccae and their immune modulating properties.

Heat-killed M. vaccae and M. vaccae Culture Filtrate.

M. vaccae (ATCC Number 15483) was cultured in sterile Medium 90 (yeast extract, 2.5 g/l; tryptone, 5 g/l; glucose 1 g/l) at 37° C. The cells were harvested by centrifugation, and transferred into sterile Middlebrook 7H9 medium (Difco Laboratories, Detroit, Mich.) with glucose at 37° C. for one day. The medium was then centrifuged to pellet the bacteria, and the culture filtrate removed. The bacterial pellet was resuspended in phosphate buffered saline at a concentration of 10 mg/ml, equivalent to $10^{10}$ M. vaccae organisms per ml. The cell suspension was then autoclaved for 15 min at 120° C. The culture filtrate was passed through a 0.45 μm filter into sterile bottles.

Preparation of Delipidated and Deglycolipidated M. vaccae (DD-M. vaccae) and Compositional Analysis.

To prepare delipidated M. vaccae, the autoclaved M. vaccae was pelleted by centrifugation, the pellet washed with water and collected again by centrifugation, and freeze-dried. An aliquot of this freeze-dried M. vaccae was set aside and referred to as lyophilised M. vaccae. When used in experiments it was resuspended in PBS to the desired concentration. Freeze-dried M. vaccae was treated with chloroform/methanol (2:1) for 60 min at room temperature to extract lipids, and the extraction was repeated once. The delipidated residue from the chloroform/methanol extraction was further treated with 50% ethanol to remove glycolipids by refluxing for two hours. The 50% ethanol extraction was repeated two times. The pooled 50% ethanol extracts were used as a source of M. vaccae glycolipids (see below). The residue from the 50% ethanol extraction was freeze-dried and weighed. The amount of delipidated and deglycolipidated M. vaccae prepared was equivalent to 11.1% of the starting wet weight of M. vaccae used. For bioassay, the delipidated and deglycolipidated M. vaccae (DD-M. vaccae), was resuspended in phosphate-buffered saline by sonication, and sterilized by autoclaving.

The compositional analyses of heat-killed M. vaccae and DD-M. vaccae are presented in Table 1. Major changes are seen in the fatty acid composition and amino acid composition of DD-M. vaccae as compared to the insoluble fraction of heat-killed M. vaccae. The data presented in Table 1 show that the insoluble fraction of heat-killed M. vaccae contains 10% w/w of lipid, and the total amino acid content is 2750 nmoles/mg, or approximately 33% w/w. DD-M. vaccae contains 1.3% w/w of lipid and 4250 nmoles/mg amino acids, which is approximately 51% w/w.

TABLE 1

Compositional analyses of heat-killed M. vaccae and DD-M. vaccae

MONOSACCHARIDE COMPOSITION

| sugar alditol | M. vaccae | DD-M. vaccae |
| --- | --- | --- |
| Inositol | 3.2% | 1.7% |
| Ribitol* | 1.7% | 0.4% |
| Arabinitol | 22.7% | 27.0% |
| Mannitol | 8.3% | 3.3% |
| Galactitol | 11.5% | 12.6% |
| Glucitol | 52.7% | 55.2% |

FATTY ACID COMPOSITION

| Fatty acid | M. vaccae | DD-M. vaccae |
| --- | --- | --- |
| C14:0 | 3.9% | 10.0% |
| C16:0 | 21.1% | 7.3% |
| C16:1 | 14.0% | 3.3% |
| C18:0 | 4.0% | 1.5% |
| C18:1* | 1.2% | 2.7% |
| C18:1w9 | 20.6% | 3.1% |
| C18:1w7 | 12.5% | 5.9% |
| C22:0 | 12.1% | 43.0% |
| C24:1* | 6.5% | 22.9% |

The insoluble fraction of heat-killed M. vaccae contains 10% w/w of lipid, and DD-M. vaccae contains 1.3% w/w of lipid.

AMINO ACID COMPOSITION

| nmoles/mg | M. vaccae | DD-M. vaccae |
| --- | --- | --- |
| ASP | 231 | 361 |
| THR | 170 | 266 |
| SER | 131 | 199 |
| GLU | 319 | 505 |
| PRO | 216 | 262 |
| GLY | 263 | 404 |
| ALA | 416 | 621 |
| CYS* | 24 | 26 |
| VAL | 172 | 272 |
| MET* | 72 | 94 |
| ILE | 104 | 171 |
| LEU | 209 | 340 |
| TYR | 39 | 75 |

TABLE 1-continued

Compositional analyses of heat-killed M. vaccae and DD-M. vaccae

| PHE | 76 | 132 |
| GlcNH2 | 5 | 6 |
| HIS | 44 | 77 |
| LYS | 108 | 167 |
| ARG | 147 | 272 |

The total amino acid content of the insoluble fraction of heat-killed M. vaccae is 2750 nmoles/mg, or approximately 33% w/w. The total amino acid content of DD-M. vaccae is 4250 nmoles/mg, or approximately 51% w/w.

M. vaccae Glycolipids

The pooled 50% ethanol extracts described above were dried by rotary evaporation, redissolve in water, and freeze-dried. The amount of glycolipid recovered was 1.2% of the starting wet weight of M. vaccae used. For bioassay, the glycolipids were dissolved in phosphate-buffered saline.

Production of Interleukin-12 From Macrophages.

Whole heat-killed M. vaccae and DD-M. vaccae were shown to have different cytokine stimulation properties. The stimulation of a Th1 immune response is enhanced by the production of interleukin-12 (IL-12) from macrophages. The ability of different M. vaccae preparations to stimulate IL-12 production was demonstrated as follows.

A group of C57BL/6J mice were injected intraperitoneally with DIFCO thioglycolate. After three days peritoneal macrophages were collected and placed in cell culture with interferon-gamma for three hours. The culture medium was replaced and, various concentrations of whole heat-killed (autoclaved) M. vaccae, lyophilized M. vaccae, DD-M. vaccae (referred to as delipidated-deglicolipidated M. vaccae in FIG. 1) and M. vaccae glycolipids were added. After a further three days at 37° C., the culture supernatants were assayed for the presence of IL-12 produced by macrophages. As shown in FIG. 1, the M. vaccae preparations stimulated the production of IL-12 from macrophages.

Figure 2:
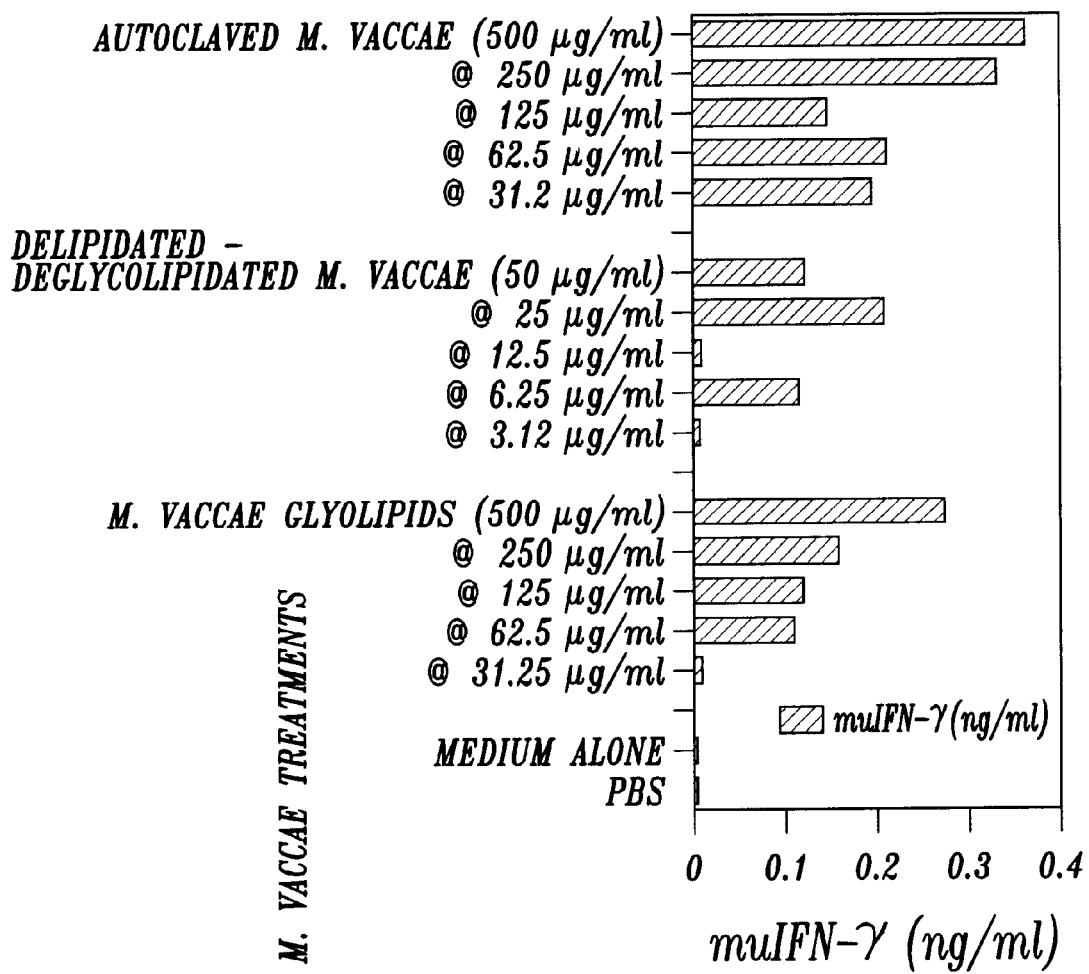
FIG. 2 compares the in vitro stimulation of interferon-gamma production in spleen cells from Severe Combined Immuno Deficient (SCID) mice by different concentrations of heat-killed (autoclaved) M. vaccae, delipidated and deglycolipidated M. vaccae, and M. vaccae glycolipids.

By contrast, these same M. vaccae preparations were examined for the ability to stimulate interferon-gamma (IFN-γ) production from Natural Killer (NK) cells. Spleen cells were prepared from Severe Combined Immunodeficient (SCID) mice. These populations contain 75–80% NK cells. The spleen cells were incubated at 37° C. in culture with different concentrations of heat-killed M. vaccae, DD-M. vaccae, or M. vaccae glycolipids. The data shown in FIG. 2 demonstrates that, while heat-killed M. vaccae and M. vaccae glycolipids stimulate production of interferon-gamma, DD-M. vaccae stimulated relatively less interferon-gamma. The combined data from FIGS. 1 and 2 indicate that, compared with whole heat-killed M. vaccae, DD-M. vaccae is a better stimulator of IL-12 than of interferon-gamma.

EXAMPLE 2

Preparation and Characterisation of Additional Derivatives of M. vaccae

Alkaline Hydrolysis of DD-M. vaccae

This procedure is intended to cleave linkages that are labile to alkaline lysis, such as the ester bonds linking mycolic acids to the arabinogalactan of the mycobacterial cell wall.

One gram of DD-M. vaccae, prepared as described in Example 1, was suspended in 20 ml of a 0.5% solution of potassium hydroxide (KOH) in ethanol. Other alkaline agents and solvents are well known in the art and may be used in the place of KOH and ethanol. The mixture was incubated at 37° C. with intermittent mixing for 48 hours. The solid residue was harvested by centrifugation, and washed twice with ethanol and once with diethyl ether. The product was air-dried overnight. The yield was 1.01 g (101%) of KOH-treated DD-M. vaccae, subsequently referred to as DD-M. vaccae-KOH (also known as Kvac). This derivative was found to be more soluble than the other derivatives of DD-M. vaccae disclosed herein.

Acid Hydrolysis of DD-M. vaccae

This procedure is intended to cleave acid-labile linkages, such as the phosphodiester bonds attaching the arabinogalactan sidechains to the peptidoglycan of the mycobacterial cell wall.

DD-M. vaccae or DD-M. vaccae-KOH (100 mg) was washed twice in 1 ml of 50 mM $H_2SO_4$ followed by resuspension and centrifugation. Other acids are well known in the art and may be used in place of sulphuric acid. For the acid hydrolysis step, the solid residue was resuspended in 1 ml of 50 mM $H_2SO_4$, and incubated at 60° C. for 72 hours. Following recovery of the solid residue by centrifugation, the acid was removed by washing the residue five times with water. The freeze-dried solid residue yielded 58.2 mg acid-treated DD-M. vaccae (DD-M. vaccae-acid; also known as Avac) or 36.7 mg acid-treated DD-M. vaccae-KOH (DD-M. vaccae-KOH-acid).

Periodic Acid Cleavage of DD-M. vaccae

This procedure is intended to cleave cis-diol-containing sugar residues in DD-M. vaccae, such as the rhamnose residue near the attachment site of the arabinogalactan chains to the peptidoglycan backbone.

DD-M. vaccae or DD-M. vaccae-KOH (100 mg) was suspended in 1 ml of a solution of 1% periodic acid in 3% acetic acid, incubated for 1 hour at room temperature and the solid residue recovered by centrifugation. This periodic acid treatment was repeated three times. The solid residue was recovered by centrifugation, and incubated with 5 ml of 0.1 M sodium borohydride for one hour at room temperature. The resulting solid residue was recovered by centrifugation and the sodium borohydride treatment repeated. After centrifugation, the solid residue was washed four times with water and freeze-dried to give a yield of 62.8 mg DD-M. vaccae-periodate (also known as Ivac) or 61.0 mg DD-M. vaccae-KOH-periodate.

Resuspension of DD-M. vaccae and DD-M. vaccae-KOH

Figure 6:
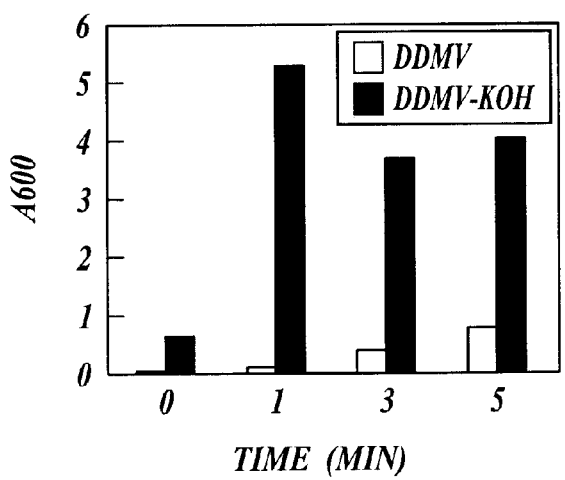
FIG. 6 illustrates the re-suspension of DD-M. vaccae and DD-M. vaccae-KOH.

DD-M. vaccae and DD-M. vaccae-KOH (11 mg each) were suspended in phosphate-buffered saline (5.5 ml). Samples were sonicated with a Virtis probe sonicator for various times at room temperature (mini-probe, 15% output). Samples were then vortexed for sixty seconds and allowed to stand for five minutes to allow the sedimentation of large particles. The absorbance of the remaining suspension at 600 nm was measured. As shown in FIG. 6, DD-M. vaccae-KOH (referred to in FIG. 6 as DDMV-KOH) was fully resuspended after one minute's sonication and further sonication produced no further increase in the absorbance. After five minutes sonication, the resuspension of DD-M. vaccae (referred to in FIG. 6 as DDMV) was still incomplete as estimated from the absorbance of the suspension. These results indicate that DD-M. vaccae-KOH is considerably more soluble than DD-M. vaccae.

Proteinase K Hydrolysis of DD-M. vaccae

This procedure is intended to digest proteins and peptides, while leaving most other materials intact.

One hundred milligrams of DD-M. vaccae, prepared as described in Example 1, was suspended in 9 ml water with sonication. Sodium dodecyl sulfate (SDS) was added to a final concentration of 1% w/v, and Proteinase K to a final concentration of 100 µg/ml w/v. The reaction mixture was incubated at 50° C. for 16 hours. The product was harvested by centrifugation, washed with phosphate-buffered saline and water, and lyophilized. The yield was 59 mg (59%) of Proteinase K-treated DD-*M. vaccae*, subsequently referred to as EVac.

Hydrofluoric Acid Hydrolysis of KOH-treated DD-*M. vaccae*

This procedure is intended to cleave linkages that are labile to hydrolysis with anhydrous hydrofluoric acid, such as glycosidic bonds, while leaving most proteins intact.

One gram of DD-*M. vaccae*-KOH, prepared as described above, was suspended in 15 ml liquid hydrogen fluoride containing anisole as a free-radical scavenger. The mixture was incubated at 0° C. with mixing for one hour. The hydrogen fluoride (HF) was removed by distillation, and the solid residue was washed with diethyl ether to remove the anisole. The product was extracted with water to yield water-soluble and water-insoluble fractions. The yield was 250 mg (25%) of water-soluble material, and 550 mg (55%) of water-insoluble HF-hydrolyzed KOH-treated DD-*M. vaccae*, subsequently referred to as HVac.

EXAMPLE 3

Effect of Immunisation With DD-*M. vaccae* and Derivatives of DD-*M. vaccae* on Asthma in Mice The ability of DD-*M. vaccae* and derivatives of DD-*M. vaccae* to inhibit the development of allergic immune responses was examined in a mouse model of the asthma-like allergen specific lung disease. The severity of this allergic disease is reflected in the large numbers of eosinophils that accumulate in the airways.

BALB/cByJ mice were given 2 µg ovalbumin in 2 mg alum adjuvant by the intraperitoneal route at time 0 and 14 days, and subsequently given 100 µg ovalbumin in 50 µl phosphate buffered saline (PBS) by the intranasal route on day 28. The mice accumulated eosinophils in their airways as detected by washing the airways of the anesthetized mice with saline, collecting the washings (broncheolar lavage or BAL), and counting the numbers of eosinophils.

Figure 3:
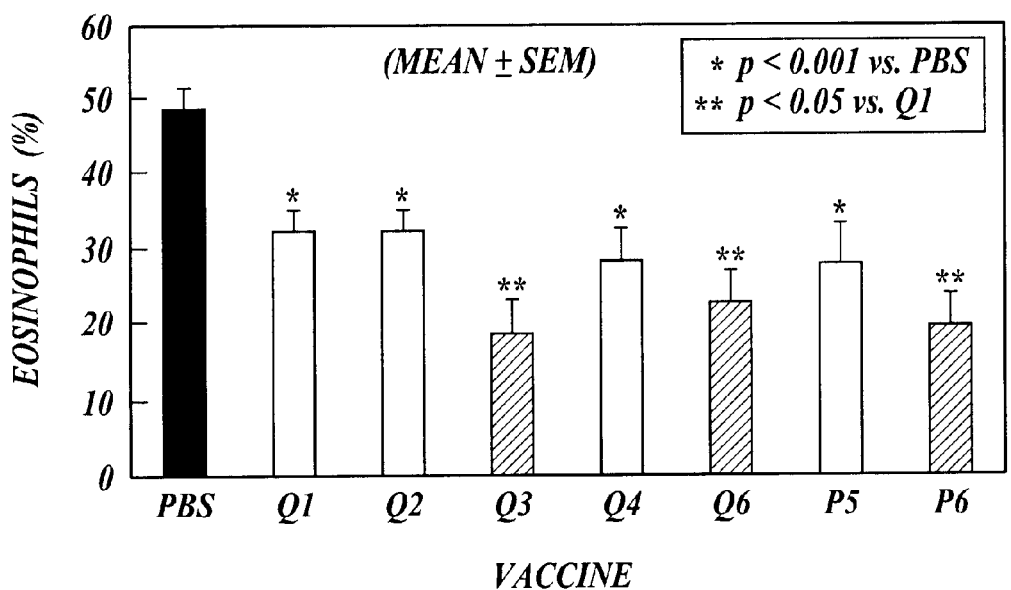
FIG. 3 shows the suppression by DD-M. vaccae (Q1) and the DD-M. vaccae derivatives Q2 (DD-M. vaccae-KOH), Q3 (DD-M. vaccae-acid), Q4 (DD-M. vaccae-periodate), Q6 (DD-M. vaccae-KOH-periodate), P5 (DD-M. vaccae-KOH-acid) and P6 (DD-M. vaccae-KOH-periodate) of ovalbumin-induced airway eosinophilia in mice vaccinated intranasally with these compounds. Control mice received PBS.

DD-*M. vaccae* derivatives were prepared as described above. Groups of 10 mice were administered 200 µg of PBS, DD-*M. vaccae* or one of the DD-*M. vaccae* derivatives (Q1: DD-*M. vaccae*; Q2: DD-*M. vaccae*-KOH; Q3: DD-*M. vaccae*-acid; Q4: *M. vaccae*-periodate; Q6 and P6: DD-*M. vaccae*-KOH-periodate; P5: DD-*M. vaccae*-KOH-acid) intranasally one week before intranasal challenge with ovalbumin. As shown in FIG. 3, statistically significant reductions were observed in the percentage of eosinophils in BAL cells collected six days after challenge with ovalbumin, compared to control mice. Furthermore, the data shows that suppression of airway eosinophilia with DD-*M. vaccae*-acid and DD-*M. vaccae*-KOH-periodate (Q3, Q6 and P6) was greater than that obtained with DD-*M. vaccae* (Q1). Control mice were given intranasal PBS. The data in FIG. 3 shows the mean and SEM per group of mice.

Eosinophils are blood cells that are prominent in the airways in allergic asthma. The secreted products of eosinophils contribute to the swelling and inflammation of the mucosal linings of the airways in allergic asthma. The data shown in FIG. 3 indicate that treatment with DD-*M. vaccae* or derivatives of DD-*M. vaccae* reduces the accumulation of lung eosinophils, and may be useful in reducing inflammation associated with eosinophilia in the airways, nasal mucosal and upper respiratory tract. Administration of DD-*M. vaccae* or derivatives of DD-*M. vaccae* may therefore reduce the severity of asthma and diseases that involve similar immune abnormalities, such as allergic rhinitis, stopic dermatitis and eczema.

In addition, serum samples were collected from mice immunized with either heat-killed *M. vaccae* or DD-*M. vaccae* and the level of antibodies to ovalbumin was measured by standard enzyme-linked immunoassay (EIA). As shown in Table 2 below, sera from mice infected with BCG had higher levels of ovalbumin specific IgG1 than sera from PBS controls. In contrast, mice immunized with heat-killed *M. vaccae* or DD-*M. vaccae* had similar or lower levels of ovalbumin-specific IgG1. As IgG1 antibodies are characteristic of a Th2 immune response, these results are consistent with the suppressive effects of DD-*M. vaccae* on the asthma-inducing Th2 immune responses.

TABLE 2

Low Antigen-Specific IgG1 Serum Levels in Mice Immunized with Heat-killed *M. vaccae* or DD-*M. vaccae*

| Treatment Group | Serum IgG1 | |
|---|---|---|
| | Mean | SEM |
| *M. vaccae* i.n. | 185.00 | 8.3 |
| *M. vaccae* s.c. | 113.64 | 8.0 |
| DD-*M. vaccae* i.n. | 96.00 | 8.1 |
| DD-*M. vaccae* s.c. | 110.00 | 4.1 |
| BCG, Pasteur | 337.00 | 27.2 |
| BCG, Connaught | 248.00 | 46.1 |
| PBS | 177.14 | 11.4 |

EXAMPLE 4

Effect of DD-*M. vaccae* Derivatives on IL-10 Production in THP-1 Cells

IL-10 has been shown to inhibit the cytokine production of Th1 cells and play a key role in the suppression of experimentally-induced inflammatory responses in skin (Berg et al., *J. Exp. Med.* 182:99–108, 1995). More recently, IL-10 has been used successfully in two clinical trials to treat psoriatic patients (Reich et al., *J. Invest. Dermatol.* 111:1235–1236, 1998 and Asadullah et al., *J. Clin. Invest.* 101:783–794, 1998). The levels of IL-10 produced by a human monocytic cell line (THP-1) cultured in the presence of derivatives of DD-*M. vaccae* were assessed as follows.

Figure 4:
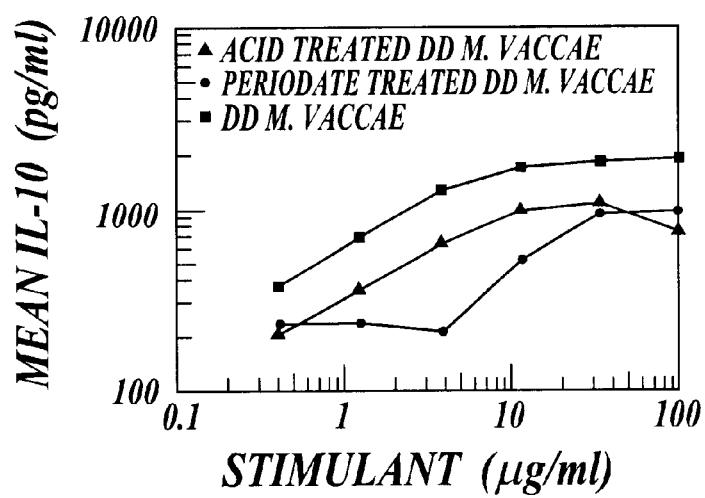
FIG. 4 shows the stimulation of IL-10 production in THP-1 cells by derivatives of DD-M. vaccae.

THP-1 cells (ATCC Number TIB-202) were cultured in RPMI medium (Gibco BRL Life Technologies) supplemented with 0.5 mg/l streptomycin, 500 U/l penicillin, 2 mg/l L-glutamine, $5 \times 10^{-5}$ M β-mercaptoethanol and 5% fetal bovine serum (FBS). One day prior to the assay, the cells were subcultured in fresh media at $5 \times 10^5$ cells/ml. Cells were incubated at 37° C. in humidified air containing 5% $CO_2$ for 24 hours and then aspirated and washed by centrifugation with 50 ml of media. The cells were resuspended in 5 ml of media and the cell concentration and viability determined by staining with Trypan blue (Sigma, St Louis Mich.) and analysis under a hemocytometer. DD-*M. vaccae* derivatives (prepared as described above) in 50 µl PBS and control stimulants were added in triplicate to wells of a 96 well plate containing 100 µl of medium and appropriate dilutions were prepared. Lipopolysaccharide (LPS) (300 µg/ml; Sigma) and PBS were used as controls. To each well, 100 µl of cells were added at a concentration of $2 \times 10^6$ cells/ml and the plates incubated at 37° C. in humidified air containing 5% $CO_2$ for 24 hours. The level of IL-10 in each well was determined using human IL-10 ELISA reagents (PharMingen, San Diego Calif.) according to the manufacturer's protocol. As shown in FIG. 4, the acid and periodate derivatives of DD-*M. vaccae* were found to stimulate significant levels of IL-10 production. The PBS control, DD-*M. vaccae*-KOH, DD-*M. vaccae*-KOH-periodate, and DD-*M. vaccae*-KOH-acid derivatives did not stimulate THP-1 cells to produce IL-10.

EXAMPLE 5

Effect of Immunizing With *M. vaccae*, and DD-*M. vaccae* on Tuberculosis

This example illustrates the effect of immunization with heat-killed *M. vaccae* or DD-*M. vaccae* prior to challenge with M. tuberculosis.

Mice were injected intraperitoneally with one of the following preparations on two occasions three weeks apart:

a), Phosphate buffered saline (PBS, control);

b): Heat-killed *M. vaccae* (500 μg); and c) DD-*M. vaccae* (50 μg).

Three weeks after the last intraperitoneal immunization, the mice were infected with $5 \times 10^5$ live H37Rv M. tuberculosis organisms. After a further three weeks, the mice were sacrificed, and their spleens homogenized and assayed for colony forming units (CFU) of M. tuberculosis as an indicator of severity of infection.

Figure 5:
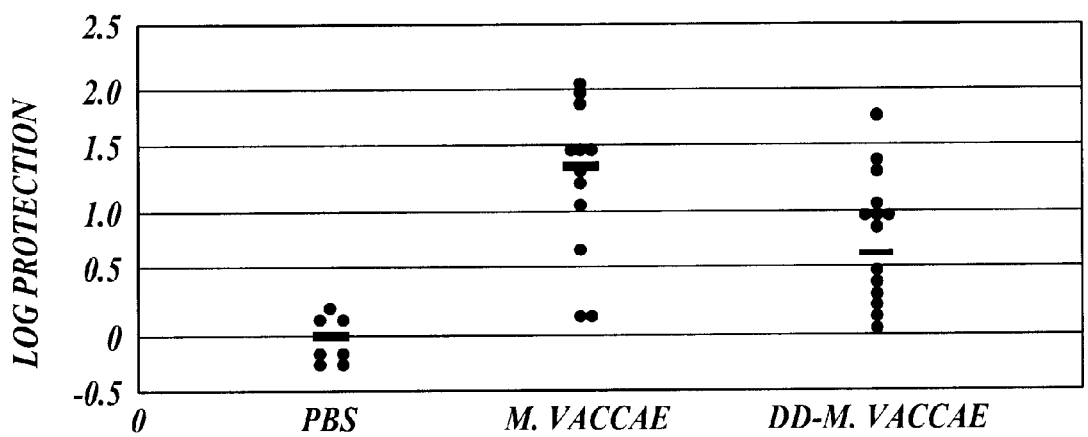
FIG. 5 illustrates the effect of immunizing mice with heat-killed M. vaccae or delipidated and deglycolipidated M. vaccae (DD-M. vaccae) prior to infection with tuberculosis.

FIG. 5 shows data in which each point represents an individual mouse. The numbers of CFU recovered from control mice immunized with PBS alone were taken as the baseline. All data from experimental mice were expressed as number of logarithms of CFU below the baseline for control mice (or log protection). As shown in FIG. 5, mice immunized with heat-killed *M. vaccae* or DD-*M. vaccae* showed respectively a mean reduction of >1 or 0.5 logs CFU. The data demonstrates the effectiveness of immunization with *M. vaccae* or DD-*M. vaccae* and indicates that DD-*M. vaccae* may be developed as a vaccine against tuberculosis.

EXAMPLE 6

Compositional Analysis of DD-*M. vaccae* and DD-*M. vaccae* Derivatives

Carbohydrate Compositional Analysis of DD-*M. vaccae* and DD-*M. vaccae* Derivatives.

The carbohydrate composition of DD-*M. vaccae* and DD-*M. vaccae* derivatives was determined using standard techniques. The results are shown in Table 3, wherein DDMV represents DD-*M. vaccae*; DDMV-KOH represents DD-*M. vaccae*-KOH; DDMV-A represents DD-*M. vaccae*-acid; DDMV-I represents DD-*M. vaccae*-periodate; DDMV-KOH-A represents DD-*M. vaccae*-KOH-acid; and DDMV-KOH-I represents DD-*M. vaccae*-KOH-periodate.

TABLE 3

Carbohydrate Compositional Analysis of DD-*M. vaccae* and DD-*M. vaccae* Derivatives

| Carbohydrate | DDMV | DDMV-KOH | DDMV-A | DDMV-I | DDMV-KOH-A | DDMV-KOH-I |
|---|---|---|---|---|---|---|
| Galactosamine | 26.6* | 29.2 | 14.9 | 37.7 | 0.3 | 3.9 |
| Glucosamine | 3.7 | 3.6 | 8.7 | 35.6 | 12.2 | 63.2 |
| Galactose | 9.7 | 9.2 | 0.7 | 3.4 | 0.0 | 0.0 |
| Glucose | 56.9 | 54.8 | 71.1 | 23.0 | 87.5 | 27.5 |
| Mannose | 3.2 | 3.2 | 4.7 | 0.4 | 0.02 | 5.5 |
| Fucose | Not detected | Not detected | Not detected | Not detected | Not detected | Not detected |

*All values in % of total carbohydrate

The results demonstrate that each of the DD-*M. vaccae* derivatives had a different carbohydrate content, as expected from the different effects of the acid, periodate or alkali treatment of the cells. In addition, DD-*M. vaccae* had a marked different carbohydrate composition when compared with the DD-*M. vaccae* derivatives. As expected, the amount of galactose in the DD-*M. vaccae*-acid and DD-*M. vaccae*-periodate derivatives was lower than in DD-*M. vaccae* and DD-*M. vaccae*-KOH. These values reflect the action of the acid and periodate in the preparation of the derivatives, cleaving the arabinogalactan sidechains from the peptidoglycan backbone.

Nucleic Acid Analysis of DD-*M. vaccae* and DD-*M. vaccae* Derivatives

Analysis by gel electrophoresis of the nucleic acid content of DD-*M. vaccae* and the DD-*M. vaccae* derivatives after treatment with Proteinase K showed that DD-*M. vaccae*, DD-*M. vaccae*-periodate and DD-*M. vaccae*-KOH contained small amounts of DNA while no detectable nucleic acid was observed for DD-*M. vaccae*-acid.

EXAMPLE 7

Effect of DD-*M. vaccae* Derivatives on IL-12 Production by Macrophages

The stimulation of a Th1 immune response is enhanced by the production of interleukin-12 (IL-12) from macrophages. The ability of different *M. vaccae* preparations to stimulate IL-12 production was demonstrated as follows.

Figure 7:
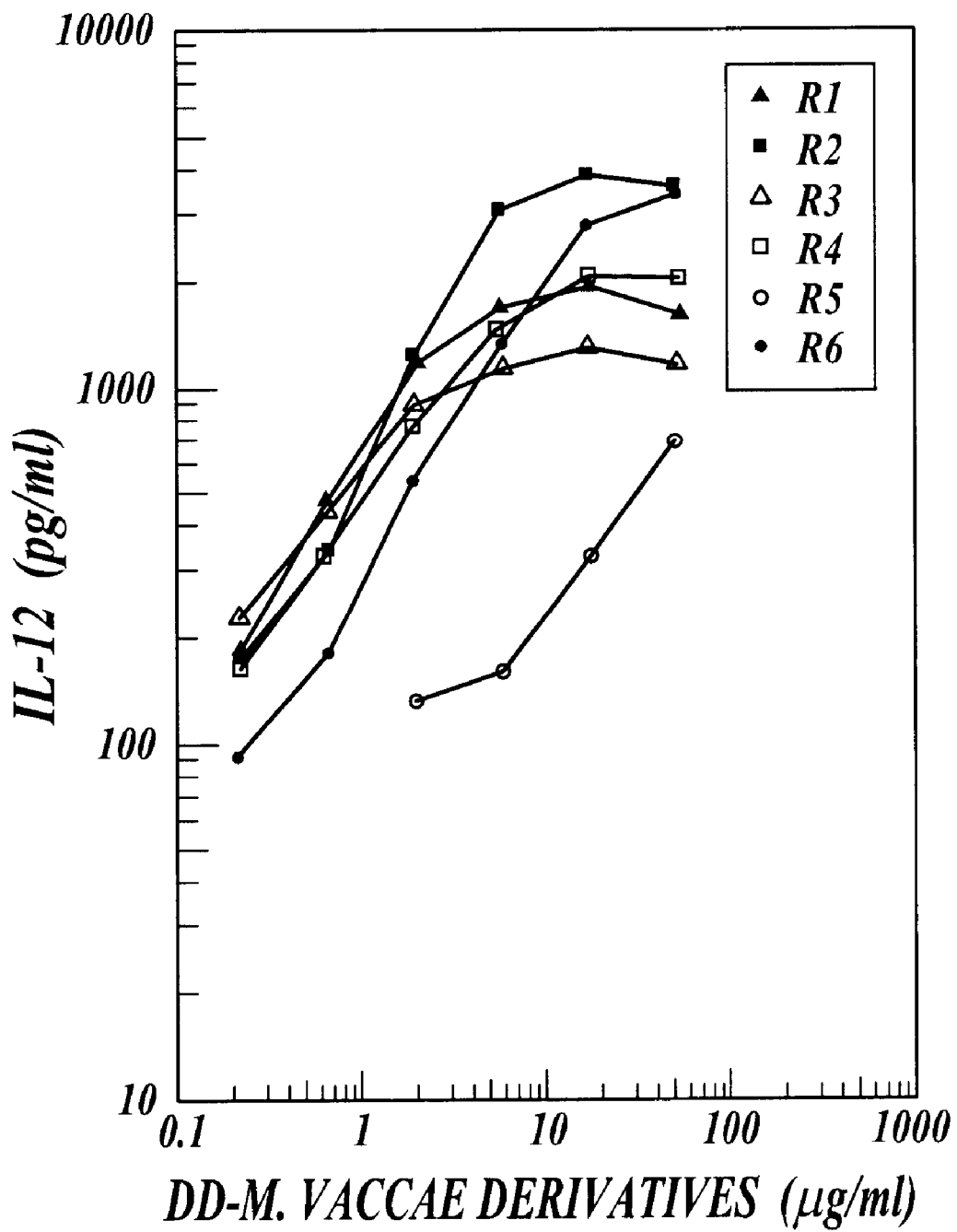
FIG. 7 shows the stimulation of IL-12 production in macrophages by DD-M. vaccae (R1) and the DD-M. vaccae derivatives DD-M. vaccae-KOH (R2), (DD-M. vaccae-acid R3), DD-M. vaccae-periodate (R4), DD-M. vaccae-KOH-acid (R5) and DD-M. vaccae-KOH-periodate (R6).

A group of BALB/cByJ nice was injected intraperitoneally with thioglycolate (Difco Laboratories, Detroit, Mich.). After three days peritoneal macrophages were collected and placed in cell culture with IFN-γ (2U/ml) for four hours. The cells were washed three times in 50 ml of cold DMEM medium (Gibco Life Technologies, Gaithersburg Md.) supplemented with 110 mg/l pyruvate, 116 mg/l L-arginine, 36 mg/l L-asparagine, 6 mg/l folic acid, 0.5 mg/l streptomycin, 500 U/l penicillin, 2 mg/l L-glutamine, $5 \times 10^{-5}$ M 2-mercaptoethanol and 5% fetal bovine serum (FBS), and adjusted to a concentration of $5 \times 10^6$ cells/ml. Various concentrations of DD-*M. vaccae* (referred to in FIG. 7 as R1) and DD-*M. vaccae*-KOH (referred to in FIG. 7 as R2), DD-*M. vaccae*-acid (referred to in FIG. 7 as R3), DD-*M. vaccae*-periodate (referred to in FIG. 7 as R4), DD-*M. vaccae*-KOH-acid (referred to in FIG. 7 as R5), and DD-*M. vaccae*-KOH-periodate (referred to in FIG. 7 as P6) were added. To each well, 0.1 ml of IFN-γ-treated macrophages were added at a concentration of $5 \times 10^6$ cells/ml. After a further 24 hours incubation at 37° C., the culture supernatants were harvested and assayed for the presence of IL-12 produced by macrophages. The level of IL-12 production by macrophages stimulated with the DD-*M. vaccae* derivatives are shown in FIG. 7. The data indicates that the DD-*M. vaccae* derivatives stimulated IL-12 production by macrophages at approximately the same level as DD-*M. vaccae*, with the exception of DD-*M. vaccae*-KOH-acid, which induced less IL-12 production.

EXAMPLE 8

Effect of Immunizing Mice With Different Dosages of DD-*M. vaccae* Derivatives This example illustrates the effect of immunization with different dosages of DD-*M. vaccae* derivatives on the development of an allergic immune response in the lungs. This was demonstrated in a mouse model of the asthma-like allergen-specific lung disease. The severity of this allergic disease is reflected in the large numbers of eosinophils that accumulate in the airways.

BALB/cByJ female mice were sensitized to ovalbumin (OVA) by intraperitoneal injection of 200 µl of an emulsion containing 10 µg OVA and 1 mg Alum adjuvant on days 0 and 7. On days 14 and 21, mice were anesthetized and vaccinated intranasally or intradermally with 200 µg of DD-*M. vaccae*-acid or PBS. On days 28 and 32, mice were anesthetized and challenged intranasally with 100 µg OVA. Mice were sacrificed on day 35 and bronchoalveolar lavage (BAL) performed using PBS. BAL cell samples were analyzed by flow cytometry to determine the eosinophils content (% eosinophils). Total BAL eosinophils numbers were obtained by multiplying the percentage eosinophils value by the total number of leukocytes obtained, with the latter value being determined using a hemacytometer.

Figure 8:
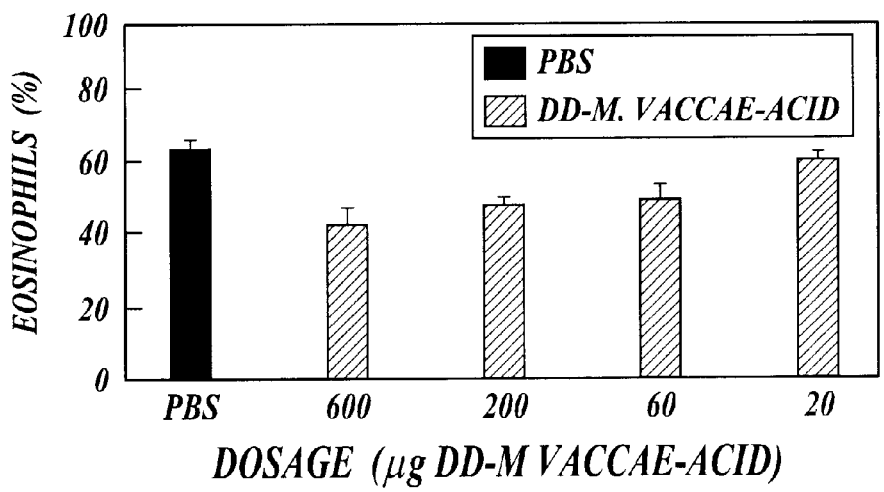
FIG. 8 illustrates the suppression of airway eosinophilia in a dose-dependent manner by a DD-M. vaccae-acid derivative.

As can be seen in FIG. 8, DD-*M. vaccae*-acid caused a significant, dosage-dependent suppression of airway eosinophilia (% eosinophils), with increasing levels of suppression being observed with increasing dosages of DD-*M. vaccae*-acid.

EXAMPLE 9

Effects of the Route of Immunization of Mice With Derivatives of DD-*M. vaccae*

This example illustrates the effect of different routes of immunization with DD-*M. vaccae* derivatives on the suppression of eosinophilia in the airways in a mouse model of the asthma-like allergen-specific lung disease.

BALB/cByJ female mice were sensitized to OVA by intraperitoneal injection of 200 µl of an emulsion containing 10 µg OVA and 1 mg Alum adjuvant on days 0 and 7. On days 14 and 21, mice were anesthetized and vaccinated intranasally or intradermally with 200 µg of DD-*M. vaccae*-acid or PBS. On days 28 and 32, mice were anesthetized and challenged intranasally with 100 µg OVA. Mice were sacrificed on day 35 and bronchoalveolar lavage (BAL) performed using PBS. BAL cell samples were analyzed by flow cytometry to determine the eosinophil content (% eosinophils). Total BAL eosinophils numbers were obtained by multiplying the percentage eosinophil value by the total number of leukocytes obtained, with the latter value being determined using a hemacytometer.

Figure 9:
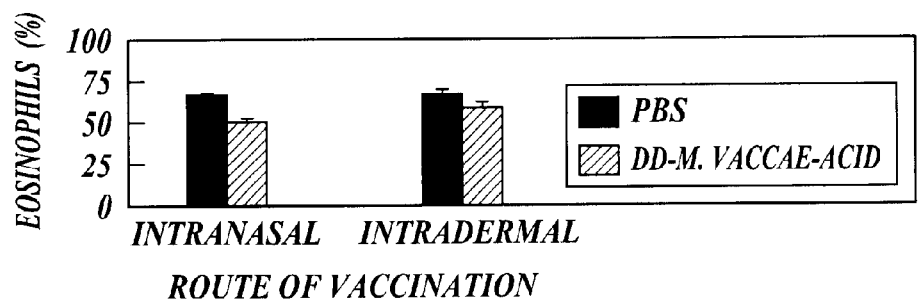
FIG. 9 compares the effect of intranasal and intradermal immunization with DD-M. vaccae-acid on the suppression of lung eosinophils.

As shown in FIG. 9, significant reductions were observed in the percentage of eosinophils in BAL cells, collected six days after challenge with ovalbumin from mice immunized intranasally with DD-*M. vaccae*-acid, compared to control mice. Furthermore, the data shows that suppression of airway eosinophilia with DD-*M. vaccae*-acid administered intranasally was greater than that seen when mice were immunized intradermally. Control mice were given intranasal PBS. The data in FIG. 9 shows the mean and SEM per group of mice.

EXAMPLE 10

Preparation and Compositional Analysis of Delipidated and Deglycolipidated M. Tuberculosis (DD-M. Tuberculosis) and *M. smegmatis* (DD-*M. smegmatis*)

M. Tuberculosis and *M. smegmatis* Culture Filtrate

Cultures of *Mycobacteriun smegmatis* (*M. smegmatis*, ATCC Number 27199) were grown as described in Example 1 for *M. vaccae* in Medium 90 with 1% added glucose. After incubation at 37° C. for 5 days, the cells were harvested by centrifugation and the culture filtrate removed. The bacterial pellet was resuspended in phosphate buffered saline at a concentration of 10 mg/ml, equivalent to $10^{10}$ *M. smegmatis* organisms per ml. The cell suspension was then autoclaved for 15 min at 120° C. The culture filtrate was passaged through a 0.45 µm filter into sterile bottles.

Cultures of M. tuberculosis strain H37Rv (ATCC Number 27294) were grown at 37° C. in GAS medium (0.3 g Bactocasitone (Difco Laboratories, Detroit Mich.), 0.05 g ferric ammonium citrate, 4 g $K_2HPO_4$, 2 g citric acid, 1 g L-alanine, 1.2 g $MgCl_2.6H_2O$, 0.6 g $K_2SO_4$, 2 g $NH_4Cl$, 1.8 ml NaOH (10 N), 5 ml glycerol, pH 7.0) for five days. Harvesting and further treatment of cells are as described above for *M. smegmatis* cells.

Preparation of Delipidated and Deglycolipidated M. Tuberculosis (DD-M. Tuberculosis) and Delipidated and Deglycolipidated *M. smegmatis* (DD-*M. smegmatis*) and Compositional Analysis.

To prepare delipidated and deglycolipidated M. tuberculosis (DD-M. tuberculosis) and *M. smegmatis* (DD-*M. smegmatis*), autoclaved M. tuberculosis and *M. smegmatis* were pelleted by centrifugation, the pellet washed with water and collected again by centrifugation, and freeze-dried. An aliquot of this freeze-dried M. tuberculosis and *M. smegmatis* was set aside and referred to as lyophilized M. tuberculosis and *M. smegmatis*, respectively: When used in experiments the lyophilized material was resuspended in PBS to the desired concentration.

Delipidated and deglycolipidated M. tuberculosis and *M. smegmatis* were prepared as described in Example 1 for the preparation of DD-*M. vaccae*. For bioassay, the freeze-dried DD-M. tuberculosis and DD-*M. smegmatis* were resuspended in phosphate-buffered saline (PBS) by sonication, and sterilized by autoclaving.

The compositional analyses of DD-M. tuberculosis and DD-*M. smegmatis* are presented in Table 4 and Table 5. Major differences are seen in some components of the monosaccharide composition of DD-M. tuberculosis and DD-*M. smegmatis* compared with the monosaccharide composition of DD-*M. vaccae*. The data presented in Table 4 show that DD-M. tuberculosis and DD-*M. smegmatis* contain 1.3% and 0.0 mol % glucose, respectively, compared with 28.1 mol % for DD*M. vaccae*.

The amino acid composition of DD-M. tuberculosis and DD-*M. smegmatis* is presented in Table 5. DD-M. tuberculosis contains 6537.9 nmoles/mg amino acids, or approximately 78.5% w/w, and DD-*M. smegmatis* contains 6007.7 nmoles/mg amino acids, which is approximately 72.1% w/w protein. When compared with the amino acid analysis of DD-*M. vaccae* given in Table 1, DD-M. tuberculosis and DD-*M. smegmatis* contain more total % protein than DD-*M. vaccae* (55.1%).

TABLE 4

Monosaccharide Composition of DD-*M. tuberculosis* and DD-*M. smegmatis*

| Monosaccharide | M. tuberculosis | | M. smegmatis | |
| --- | --- | --- | --- | --- |
| | wt % | mol % | wt % | mol % |
| Insitol | 0.0 | 0.0 | 0.0 | 0.0 |
| Glycerol | 9.5 | 9.7 | 15.2 | 15.5 |
| Arabinose | 69.3 | 71.4 | 69.3 | 70.0 |
| Xylose | ND* | ND | 3.9 | 4.0 |
| Mannose | 3.5 | 3.0 | 2.2 | 1.9 |
| Glucose | 1.5 | 1.3 | 0.0 | 0.0 |
| Galactose | 12.4 | 10.7 | 9.4 | 8.0 |

*Not done

TABLE 5

Amino Acid Composition of DD-*M. tuberculosis* and DD-*M. smegmatis*

| | M. tuberculosis | | M. smegmatis | |
| --- | --- | --- | --- | --- |
| Amino acid | Total Protein nmoles/mg | Total % protein | Total Protein nmoles/mg | Total % protein |
| ASP | 592.5 | 9.1 | 557.0 | 9.3 |
| THR | 348.1 | 5.3 | 300.5 | 5.0 |
| SER | 218.6 | 3.3 | 252.6 | 4.2 |
| GLU | 815.7 | 12.5 | 664.9 | 11.1 |
| PRO | 342.0 | 5.2 | 451.9 | 7.5 |
| GLY | 642.9 | 9.8 | 564.7 | 9.4 |
| ALA | 927.9 | 14.2 | 875.1 | 14.6 |
| CYS | 31.8 | 0.5 | 20.9 | 0.3 |
| VAL | 509.7 | 7.8 | 434.8 | 7.2 |
| MET | 122.6 | 1.9 | 113.1 | 1.9 |
| ILE | 309.9 | 4.7 | 243.5 | 4.1 |
| LEU | 542.5 | 8.3 | 490.8 | 8.2 |
| TYR | 116.0 | 1.8 | 108.3 | 1.8 |
| PHE | 198.9 | 3.0 | 193.3 | 3.2 |
| HIS | 126.1 | 1.9 | 117.2 | 2.0 |
| LYS | 272.1 | 4.2 | 247.8 | 4.1 |
| ARG | 421.0 | 6.4 | 371.7 | 6.2 |

EXAMPLE 11

Effects of Immunization With DD-M. tuberculosis and DD-*M. smegmatis* on Asthma in Mice The ability of DD-M. tuberculosis and DD-*M. smegmatis* to inhibit the development of allergic immune responses was examined in a mouse model of the asthma-like allergen-specific lung disease, as described above in Example 8. The results illustrate the effect of immunization with DD-M. tuberculosis and DD-*M. smegmatis* on the suppression of eosinophilia in the airways, illustrating their immune modulating properties.

BALB/cByJ female mice were sensitized to OVA by intraperitoneal injection of 200 μl of an emulsion containing 10 μg OVA and 1 mg Alum adjuvant on days 0 and 7. On days 14 and 21, mice were anesthetized and vaccinated intranasally or intradermally with 200 μg of DD-*M. vaccae*, DD-M. tuberculosis, DD-*M. smegmatis* or PBS. On days 28 and 32, mice were anesthetized and challenged intranasally with 100 μg OVA. Mice were sacrificed on day 35 and bronchoalveolar lavage (BAL) performed using PBS. BAL cell samples were analyzed by flow cytometry to determine the eosinophil content (% eosinophils). Total BAL eosinophil numbers were obtained by multiplying the percentage eosinophil value by the total number of leukocytes obtained, with the latter value being determined using a hemacytometer.

Figure 10:
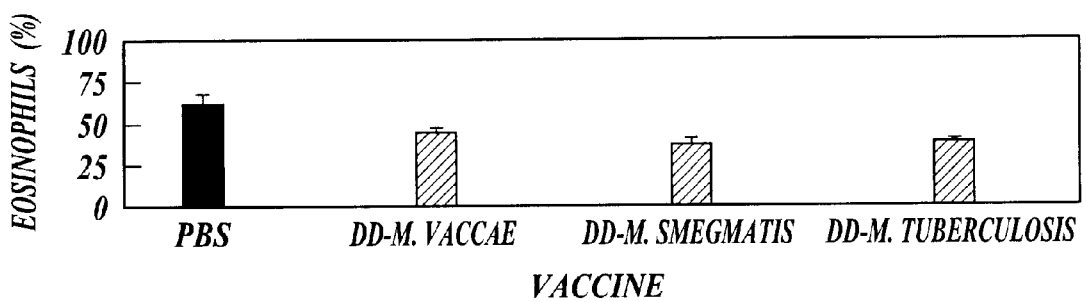
FIG. 10 illustrates the effect of immunization with DD-M. vaccae, DD-M. tuberculosis and DD-M. smegmatis on airway eosinophilia.

The data shown in FIG. 10 indicate that treatment with DD-M. tuberculosis and DD-*M smegmatis* reduces the accumulation of lung eosinophils similar to the reduction following immunization with DD-*M. vaccae*, and that DD-M. tuberculosis and DD-*M. smegmatis* may be useful in reducing inflammation associated with eosinophilia in the airways, nasal mucosal and upper respiratory tract. Administration of DD-M. tuberculosis and DD-*M. smegmatis* may therefore reduce the severity of asthma and diseases that involve similar immune abnormalities, such as allergic rhinitis.

EXAMPLE 12

Effects of DD-*M. vaccae* on Production of IL-10, TNF-Alpha and IFN-Gamma in Human Peripheral Blood Mononuclear Cells This example describes studies on the ability of DD-*M. vaccae* to stimulate cytokine production in human peripheral blood mononuclear cells (PBMC).

Human blood was separated into PBMC and non-adherent cells, and the cytokine production of each fraction determined after stimulation with DD-*M. vaccae* as follows. Blood was diluted with an equal volume of saline and 15–20 ml was layered onto 10 ml Ficoll (Gibco BRL Life Technologies, Gaithersburg, Md.). The lymphocyte layer was removed after centrifugation at 1,800 rpm for 20 min, washed three times in RPMI medium (Gibco BRL) and counted using Trypan blue. Cells were resuspended in RPMI containing 5% heat-inactivated autologous serum at a concentration of $2 \times 10^6$ per ml. The cell sample was divided to prepare non-adherent cells.

Non-adherent cells were prepared by incubating 20 ml of the lymphocytes in RPMI supplemented with serum (as above) for one hour in a humidified atmosphere containing 5% $CO_2$. The non-adherent cells were transferred to a fresh flask and the incubation repeated once more. The non-adherent cells were removed, counted and resuspended at a concentration of $2 \times 10^6$ per ml in supplemented RPMI medium. Serial dilutions of DD-*M. vaccae* were prepared starting at 200 μg/ml and added to 100 μl medium (supplemented RPMI) in a 96-well plate. PBMC and non-adherent cells were added to the wells (100 μl) and the plates incubated at 37° C. for 48 hours in a humidified atmosphere containing 5% $CO_2$. A 150 μl aliquot was removed from each well to determine the amount of cytokine produced by the different cells after stimulation with DD-*M. vaccae*.

Figure 11:
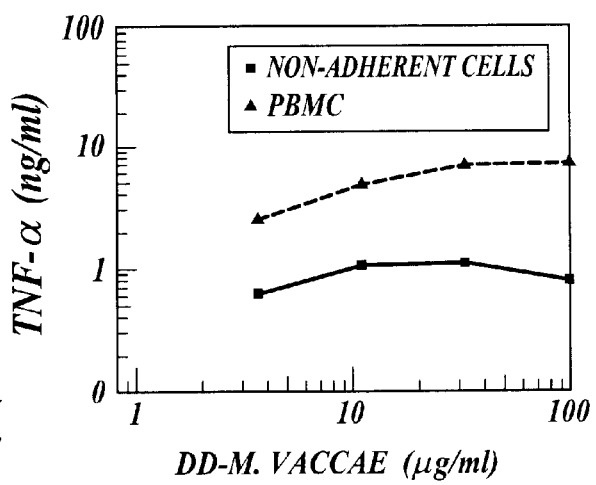
FIG. 11 illustrates TNF-α production by human PBMC and non-adherent cells stimulated with DD-M. vaccae.
Figure 12A:
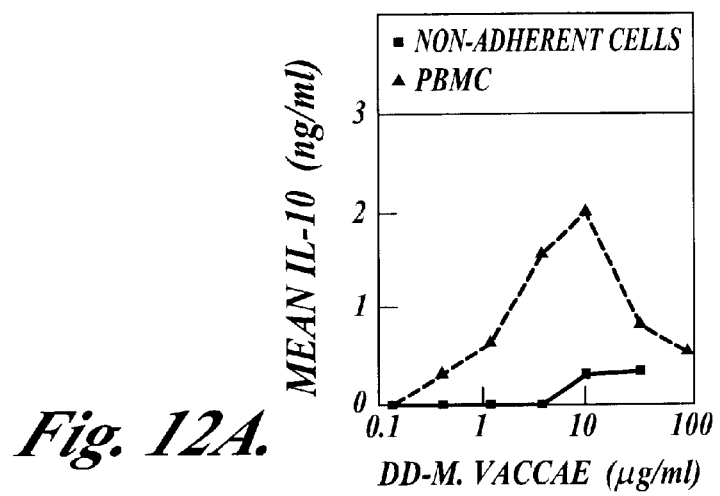
FIGS. 12A and 12B illustrate IL-10 and IFN-γ production, respectively, by human PBMC and non-adherent cells stimulated with DD-M. vaccae.
Figure 12B:
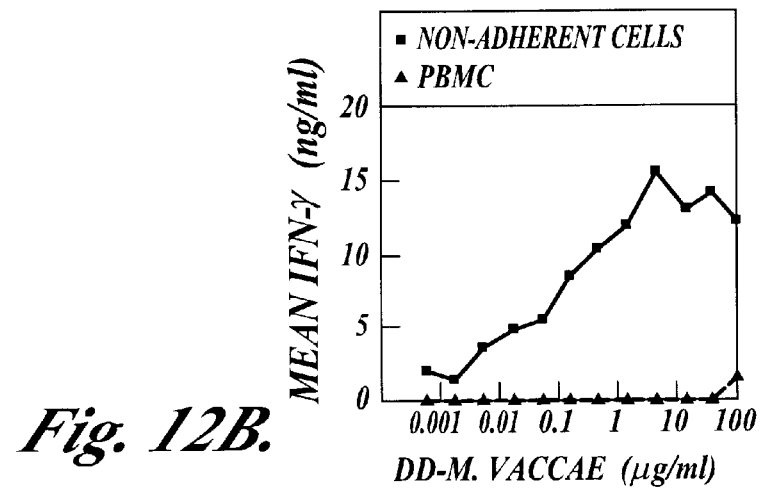

DD-*M. vaccae* stimulated PBMC to secrete TNF-α and IL-10 (FIGS. 11 and 12A, respectively), but stimulated the non-adherent cells to produce IFN-γ (FIG. 12B). These data suggest that INF-γ production in DD-*M. vaccae*-stimulated PBMC is repressed by the simultaneous secretion of IL-10.

EXAMPLE 13

Activation of T Cells By Heat-killed *M. vaccae* and DD-*M. vaccae*

The ability of heat-killed *M. vaccae* and DD-*M. vaccae* to activate human T cells and Natural Killer (NK) cells was examined as follows.

Human peripheral blood mononuclear cells (PBMC) at a concentration of $5 \times 10^6$ cells per ml were cultured with 20 μg/ml of either heat-killed *M. vaccae* or DD-*M. vaccae* for 24 hours. Control cells were cultured with media alone. Cultured cells were then stained with monoclonal antibodies against CD56 (a marker for NK cells), αβT cells, or γδT cells in combination with monoclonal antibody against CD69, a molecule expressed by activated cells. The cells were then analyzed by flow cytometry. The percentage of cells expressing CD69 are provided in Table 6.

TABLE 6

Activation of Human T Cells and NK Cells by Heat-Killed *M. vaccae* and DD-*M. vaccae*

|  | αβT cells | γδT cells | NK cells |
|---|---|---|---|
| Control | 3.8 | 6.2 | 4.8 |
| Heat-killed *M. vaccae* | 8.3 | 10.2 | 40.3 |
| DD-*M. vaccae* | 10.1 | 17.5 | 49.9 |

These results indicate that heat-killed *M. vaccae* and DD-*M. vaccae* activate both αβ and γδ T cells, as well as NK cells.

Recent studies by Holt and Sly (*Nature Medicine* 5:1127–1128, 1999) indicate that, in asthma, γδ T cells are important in maintaining normal airway responsiveness and down regulate airway responsiveness to allergen challenge, possibly by controlling the "repair" response of the airway epithelium to γδ T cells cell-mediated damage. Since *M. vaccae* and DD-*M. vaccae* are able to activate γδ T cells, they are likely to effective in restoring a normal epithelium in diseased areas of the body where γδ T cells are found, such as airways, lungs, skin and gut.

EXAMPLE 14

Effects of Immunization With DD-*M. vaccae*-Acid, *M. vaccae*, Hvac and Evac on Asthma in Mice This example illustrates the effect of immunization with DD-*M. vaccae* and the DD-*M. vaccae* derivatives DD-*M. vaccae*-acid, Hvac and Evac on the development of an allergic immune response in the lungs. This was demonstrated in a mouse model of the asthma-like allergen specific lung disease. The severity of this allergic disease is reflected in the large numbers of eosinophils that accumulate in the airways.

BALB/cByJ female mice were sensitized to OVA by intraperitoneal injection of 200 μl of an emulsion containing 10 μg OVA and 1 mg Alum adjuvant on days 0 and 7. On days 14 and 21, mice were anesthetized and vaccinated intranasally or intradermally with 200 μg of DD-*M. vaccae*, DD-*M. vaccae*-acid, Hvac, Evac or PBS. On days 28 and 32, mice were anesthetized and challenged intranasally with 100 μg OVA in 50 μl PBS. Mice were sacrificed on day 35 and bronchoalveolar lavage (BAL) performed using PBS. BAL cell samples were analyzed by flow cytometry to determine the eosinophil content (% eosinophils). Total BAL eosinophil numbers were obtained by multiplying the percentage eosinophil value by the total number of leukocytes obtained, with the latter value being determined using a hemacytometer.

Figure 13:
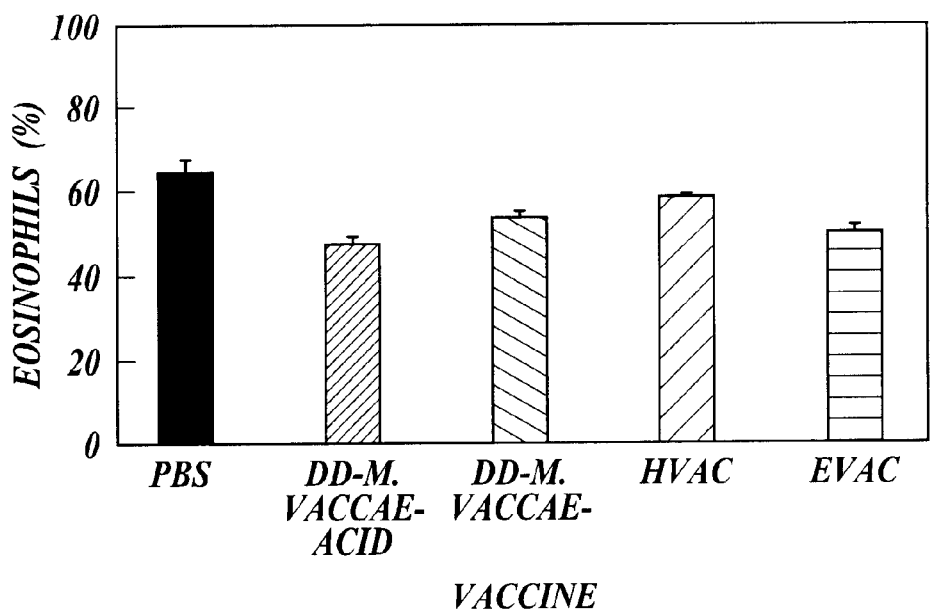
FIG. 13 illustrates the suppression of allergen-induced airway eosinophilia by DD-M. vaccae and the DD-M. vaccae derivatives referred to as DD-M. vaccae-acid, Hvac and Evac.

As can be seen in FIG. 13, DD-*M. vaccae*, Hvac and Evac caused a significant suppression of airway eosinophilia (expressed as % eosinophils).

EXAMPLE 15

Suppression of Airway Eosinophilia DD-*M. vaccae*-Acid Administered After Challenge With OVA This example illustrates the effect of DD-*M. vaccae*-acid on the development of an allergic immune response in the lungs as demonstrated in a mouse model of the asthma-like allergen specific lung disease The DD-*M. vaccae*-acid was administered three days after challenge with OVA to induce severe airway eosinophilia.

BALB/cByJ female mice (ten mice per group) were sensitized to OVA by intraperitoneal injection of 200 μl of an emulsion containing 10 μg OVA and 1 mg Alum adjuvant on days 0 and 7. On days 14 and 18, mice were anesthetized and challenged intranasally with 100 μg OVA contained in 50 μl PBS. On day 21, mice were again anesthetized and 200 μg DD-*M. vaccae*-acid was administered intranasally. Mice were sacrificed on day 25 and BAL performed using PBS. Control mice received administration of PBS instead of DD-*M. vaccae*-acid following the same treatment regime as for the experimental mice. BAL cell samples were analyzed by flow cytometry to determine the eosinophil content (% eosinophils). Total BAL eosinophil numbers were obtained by multiplying the percentage eosinophil value by the total number of leukocytes obtained, with the latter value being determined using a hemacytometer.

Figure 14:
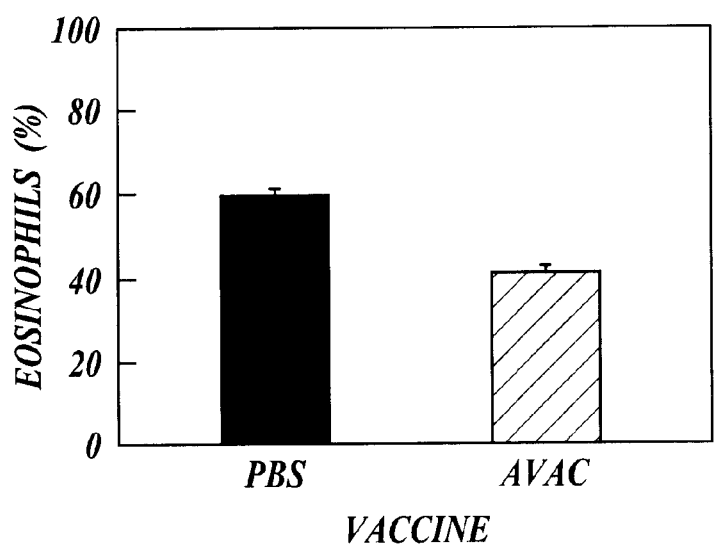
FIG. 14 illustrates the therapeutic effect of DD-M. vaccae-acid on severe allergen-induced airway eosinophilia in mice when the DD-M. vaccae-acid is administered three days after challenge with OVA.

As shown in FIG. 14, a significant suppression of airway eosinophilia (expressed as % eosinophils) was observed, illustrating the therapeutic effect of DD-*M. vaccae*-acid. In both PBS- and DD-*M. vaccae*-acid-treated mice, the severity of airway eosinophilia decreased as the time interval between the two OVA-challenges increased. Furthermore, DD-*M. vaccae*-acid caused statistically significant suppression of % eosinophil values in all three groups of mice used. This data demonstrates that DD-*M. vaccae*-acid has therapeutic benefit when administered after induction of airway eosinophilia.

EXAMPLE 16

Suppression of Airway Eosinophilia by DD-*M. vaccae*-Acid Administered Immediately Before Challenge With OVA This example illustrates the therapeutic effect of one or two administrations of DD-*M. vaccae*-acid one day before two challenges with OVA to induce severe airway eosinophilia in the mouse model of the asthma-like allergen-specific lung disease.

Two groups of BALB/cByJ female mice were sensitized to OVA by intraperitoneal injection of 200 μl of an emulsion containing 10 μg OVA and 1 mg Alum adjuvant on days 0 and 7. On day 14, mice were anesthetized and DD-*M. vaccae*-acid (200 μg) was administered intranasally. On day 15, mice were anesthetized and challenged intranasally with 100 μg OVA contained in 50 μl PBS. Mice in Group I received a second intranasal OVA challenge with 100 μg OVA in 50 μl PBS on day 19. Mice in Group II received a second administration of 200 μg DD-*M. vaccae*-acid on day 18, followed by a second OVA challenge (100 μg OVA in 50 μl PBS) on day 19. The mice from both groups were sacrificed on day 22 and BAL performed using PBS. Two groups of control mice were immunized with PBS instead of DD-*M. vaccae*-acid following the same treatment regime as the experimental groups. BAL cell samples were analyzed by flow cytometry to determine the eosinophil content (% eosinophils). Total BAL eosinophil numbers were obtained by multiplying the percentage eosinophil value by the total number of leukocytes obtained, with the latter value being determined using a hemacytometer.

Figure 15:
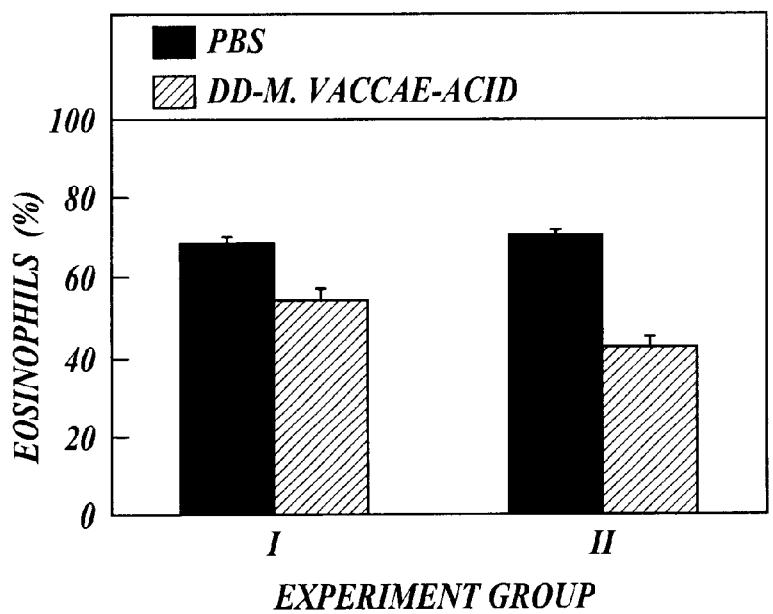
FIG. 15 illustrates the suppressive effect of DD-M. vaccae-acid on allergen-induced airway eosinophilia when the DD-M. vaccae-acid is administered immediately prior to either one or two challenges with OVA.

As can be seen in FIG. 15, a statistically significant suppression (p=0.0000015) of airway eosinophilia (expressed as % eosinophils) was observed, illustrating the therapeutic effect of DD-*M. vaccae*-acid. When mice were treated with DD-*M. vaccae*-acid prior to the first challenge only, the percent eosinophil values were reduced by 20%. Suppression of airway eosinophilia was enhanced when mice were treated with DD-*M. vaccae*-acid prior to both challenges, as indicated by the reduction of percent eosinophil values by 40%.

EXAMPLE 17

Suppression of Airway Eosinophilia DD-*M. vaccae*-Acid Administered After Challenge With OVA This example illustrates the therapeutic effect of two immunizations with the DD-*M. vaccae* derivative DD-*M. vaccae*-acid three days after challenge with OVA on the development of an allergic immune response in the lungs in the mouse model of the asthma-like allergen-specific lung disease.

Three groups of BALB/cByJ female mice were sensitized to OVA by intraperitoneal injection of 200 µl of an emulsion containing 10 µg OVA and 1 mg Alum adjuvant on days 0 and 7. On days 14, all mice were anesthetized and challenged intranasally with 100 µg OVA contained in 50 µl PBS. On day 18, all mice were again anesthetized and 200 µg DD-*M. vaccae*-acid was administered intranasally. Mice from Group 1 were challenged with a second intranasal administration of OVA (100 µg in 50 µl PBS) on day 21 (seven days after the first challenge). These mice were sacrificed on day 24 and BAL performed using PBS. Mice from Group II received the second OVA challenge on day 25 (11 days after the first challenge), were sacrificed on day 28 and BAL performed using PBS. Mice from Group III received a second administration of 200 µg of DD-*M. vaccae*-acid on day 25. These mice were then challenged on day 28 with a second administration of 100 µg OVA in 50 µl PBS (14 days after the first challenge), sacrificed on day 31 and BAL performed using PBS. Three groups of control mice received PBS instead of DD-*M. vaccae*-acid intranasally following the same immunization regime as the experimental groups. BAL cell samples were analyzed by flow cytometry to determine the eosinophil content (% eosinophils). Total BAL eosinophil numbers were obtained by multiplying the percentage eosinophil value by the total number of leukocytes obtained, with the latter value being determined using a hemacytometer.

Figure 16:
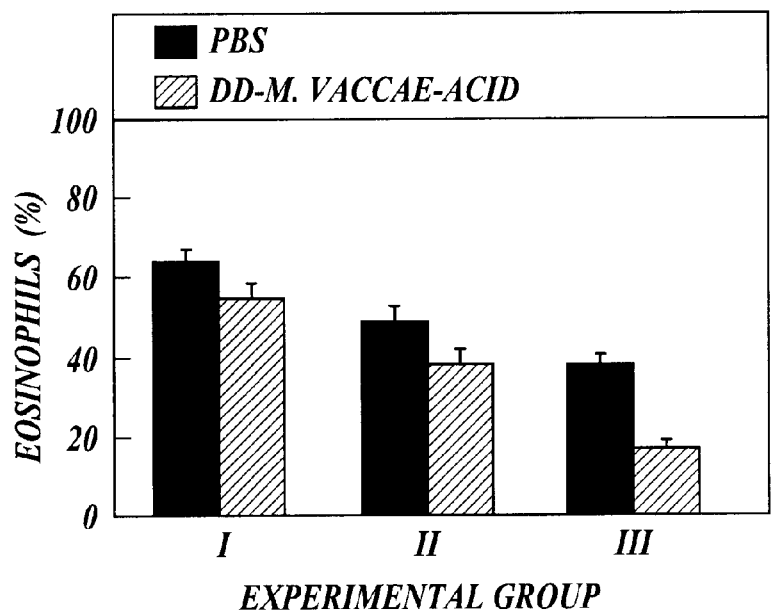
FIG. 16 illustrates the effect of DD-M. vaccae-acid on the suppression of allergen-induced eosinophilia in mice when the DD-M. vaccae-acid is administered either once or twice between the first and second challenges with OVA.

As shown in FIG. 16, a statistically significant suppression of airway eosinophilia (expressed as % eosinophils) was observed, illustrating the therapeutic effect of DD-*M. vaccae*-acid. In both PBS- and DD-*M. vaccae*-acid-treated mice, the severity of airway eosinophilia decreased as the time interval between the two OVA-challenges increased. Further, DD-*M. vaccae*-acid caused a statistically significant suppression of % eosinophil values in all three protocols followed.

In mice treated with DD-*M. vaccae*-acid four days after the first challenge, followed by a second challenge three days later (challenge delay=7 days), airway eosinophilia was reduced by about 15% (Group I; p=0.034). When the second challenge was delayed for a further four days, a slightly greater degree of suppression (approx. 25%) was observed (Group II; p=0.036). When mice were treated with DD-*M. vaccae*-acid twice prior to the second challenge, airway eosinophilia was suppressed by 56% (Group III; p=0.0000027). This data shows that DD-*M. vaccae*-acid has a therapeutic effect when administered after induction of airway eosinophilia.

EXAMPLE 18

Inhibitory Effect of DD-*M. vaccae*-Acid on Development of Allergic Airway Disease When Administered During Exposure of Sensitive Mice to Allergen This example illustrates the therapeutic effect of DD-*M. vaccae*-acid on the development of allergic airway disease in a mouse model of asthma-like allergen-specific lung disease when administered during exposure of sensitive mice to an allergen.

Two groups of 8 female BALB/cByJ mice each were immunized intraperitoneally at six and again at seven weeks of age, with an emulsion of chicken egg ovalbumin (OVA, 10 µg per mouse) and aluminium hydroxide (Alum, 1 mg per rouse) in phosphate buffered saline (PBS). At eight and again at nine weeks of age, mice in Group 1 were given 50 µl of PBS containing 100 µg OVA intranasally, and mice in Group 2 were given 50 µl PBS containing 100 µg OVA plus 1 mg DD-*M. vaccae*-acid intranasally. At ten weeks of age, all of the mice were euthanized and the airways lavaged with three 1-ml volumes of PBS. The leukocytes in the bronchoalveolar lavage (BAL) were subsequently analyzed by flow cytometry to determine the proportion of eosinophils.

Figure 17:
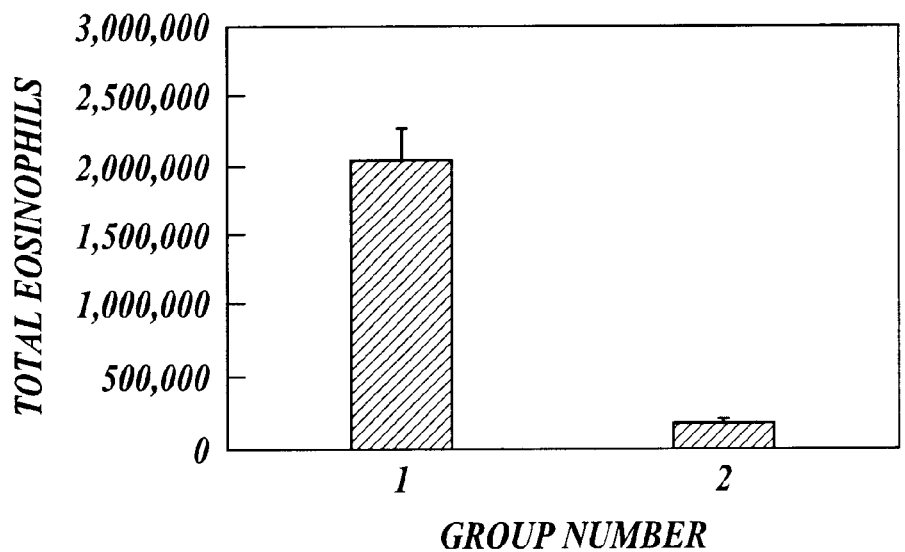
FIG. 17 illustrates the effect of DD-M. vaccae-acid on the development of allergen-induced airway eosinophilia when the DD-M. vaccae-acid is administered during exposure to OVA.

As shown in FIG. 17, mice in Group 1 developed severe allergic airways disease, with the airways of each mouse containing an average of $2.0\pm0.2\times10^6$ eosinophils (mean ±SEM, n=8). When mice were given both OVA and DD-*M. vaccae*-acid (Group 2), airway eosinophil numbers were suppressed by 91%. These data show that DD-*M. vaccae*-acid is capable of suppressing allergic airways disease when administered during exposure of sensitive mice to allergen.

EXAMPLE 19

Inhibitory Effect of DD-*M. vaccae*-Acid on Development of allergic Airway Disease When Administered During Sensitization to Allergen This example illustrates the therapeutic effect of DD-*M. vaccae*-acid on the development of allergic airway disease in a mouse model of allergen-induced asthma when administered during sensitisation to allergen.

Four groups of 10 female BALB/cByJ mice each were immunized intraperitoneally with an emulsion of OVA (10 µg per mouse) and Alum (1 mg per mouse) in PBS at six and again at seven weeks of age. Mice in Groups 2, 3, and 4 were immunized intraperitoneally with emulsions containing OVA, Alum, and either 40 µg (Group 2), 200 g (Group 3), or 1000 µg (Group 4) DD-*M. vaccae*-acid, respectively. At eight weeks of age, and again four days later, all of the mice were given 50 µl of PBS containing 100 µg OVA intranasally. At nine weeks of age all of the mice were euthanized and the airways lavaged with three 1-ml volumes of PBS. The BAL leukocytes were subsequently analyzed by flow cytometry to determine the proportion of eosinophils.

Figure 18:
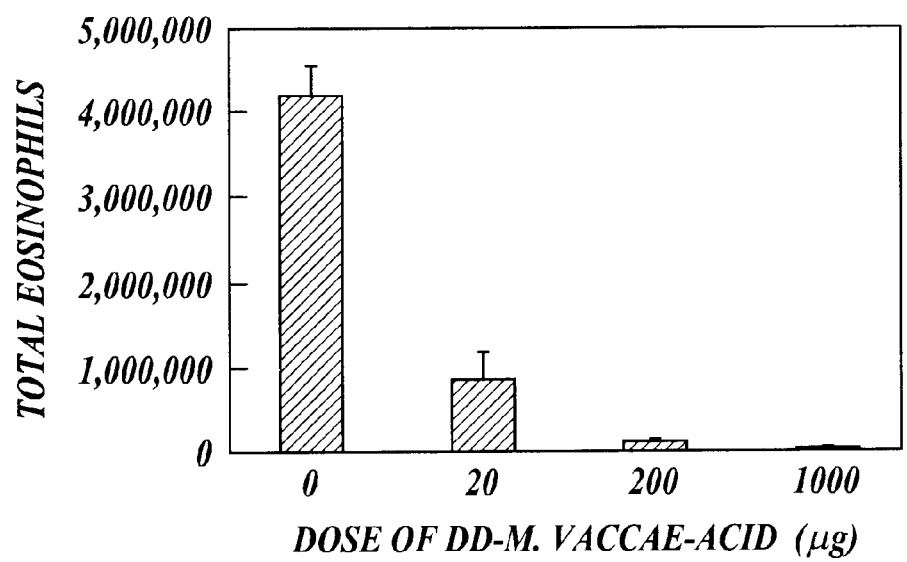
FIG. 18 illustrates the effect of DD-M. vaccae-acid on the development of allergen-induced airway eosinophilia when the DD-M. vaccae-acid is administered during sensitization to OVA.
Figure 19:
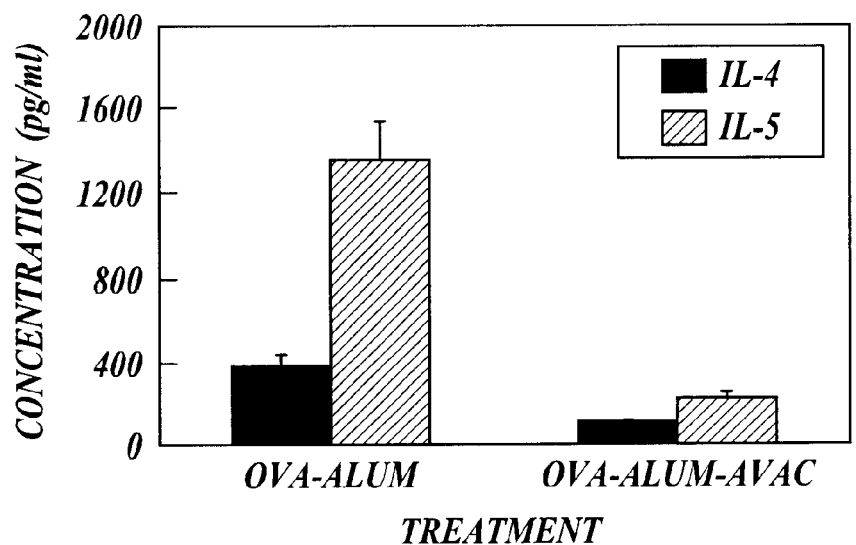
FIG. 19 illustrates the effect of DD-M. vaccae-acid on levels of IL-4 and IL-5 in bronchoelar lavage of nice at 24 hours after challenge with OVA. The DD-M. vaccae-acid is coadministered with OVA during sensitization. IL-4 and IL-5 levels were measured using enzyme linked immunoassay specific for each cytokine.
Figure 20:
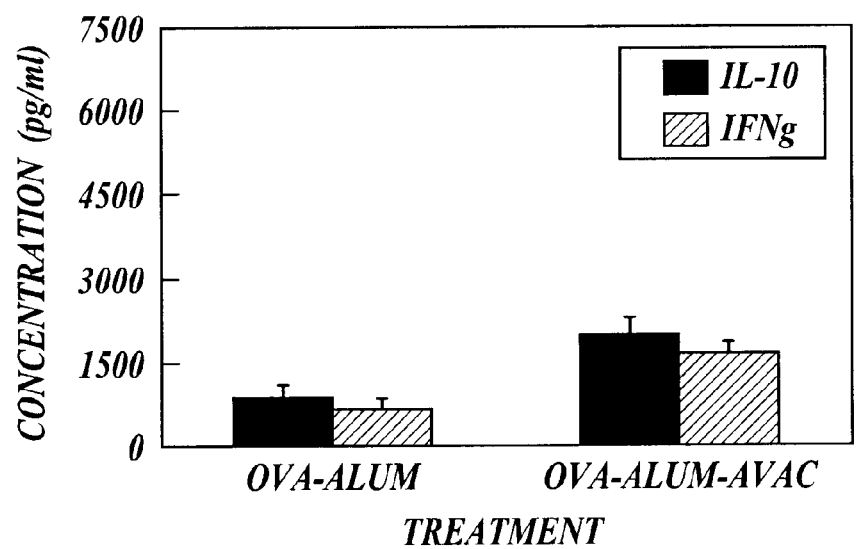
FIG. 20 illustrates the effect of DD-M. vaccae-acid on levels of IL-10 and IFN-γ content in broncheolar lavage of mice at 24 hours after challenge with OVA. The DD-M. vaccae-acid was coadministered with OVA during sensitization. IL-10 and IFN-γ levels were measured using enzyme linked immunoassay specific for each cytokine.

As shown in FIG. 18, mice in Group 1 developed severe allergic airways disease, with the airways of each mouse containing an average of $4.2\pm0.4\times10^6$ eosinophils (mean ±SEM, n=10). The results for nice in Groups 2, 3, and 4 show that co-administration of DD-*M. vaccae*-acid suppressed the development of allergic airways disease in a dose-dependent manner such that total airway eosinophil load was reduced by 99% in mice that were given a dose of 1000 µg. Thus, DD-*M. vaccae*-acid is capable of inhibiting the development of allergic airways disease when administered during sensitization to allergen.

EXAMPLE 20

Method of Using DD-*M. vaccae*-Acid (Avac) to Treat Atopic Eczema in Human Patients Male and female human patients between the ages of 16 and 70 years with atopic eczema who are not currently receiving other medications for eczema are injected intradermally at time 0 and 3 weeks later with 25–200 ug Avac in saline (50–100 ul volume) or with a placebo. The medical history of the patients is taken and a formal diagnosis of atopic eczema is made prior to the start of treatment. At this time, the patients are given a DLQI (Dermatology Life Quality Index) (*Clinical and Experimental Dermatology* 1994; 19: 210–216), a Leicester score assessment and a diary card for recording changes in symptoms of eczema and other manifestations of allergy (e.g., hayfever, asthma). Thereafter, patients are evaluated at 3 week intervals until 12 weeks after the start of treatment. Safety assessments are also made throughout the treatment period. The results are analysed for statistical validity using conventional statistical methods.

Although the present invention has been described in some detail by way of illustration and example for purposes of clarity of understanding, changes and modifications can be carried out without departing from the scope of the invention which is intended to be limited only by the scope of the appended claims.

We claim:

1. A method for the treatment of atopic dermatitis in a patient, comprising administering to the patient a composition that is effective at modulating the amount of an interleukin molecule involved in an antigen-specific Th2-mediated immune response in the patient, wherein the composition comprises delipidated and deglycolipidated *M. vaccae* cells that have been treated by acid hydrolysis.

2. The method of claim 1, wherein the composition additionally comprises an adjuvant.

3. The method of claim 1, wherein the delipidated and deglycolipidated *Mycobacterium vaccae* cells that have been treated by acid hydrolysis contain galactose in an amount less than 9.7% of total carbohydrate.

4. The method of claim 1, wherein the delipidated and deglycolipidated *Mycobacterium vaccae* cells that have been treated by acid hydrolysis contain glucosamine in an amount greater than 3.7% of total carbohydrate.

5. A method for the treatment of atopic dermatitis in a patient, comprising administering to the patient a composition comprising delipidated and deglycolipidated *Mycobacterium vaccae* cells that have been treated by acid hydrolysis.

6. The method of claim 5, wherein the composition additionally comprises an adjuvant.

7. The method of claim 5, wherein the delipidated and deglycolipidated *Mycobacterium vaccae* cells that have been treated by acid hydrolysis contain galactose in an amount less than 9.7% of total carbohydrate.

8. The method of claim 5, wherein the delipidated and deglycolipidated *Mycobacterium vaccae* cells that have been treated by acid hydrolysis contain glucosamine in an amount greater than 3.7% of total carbohydrate.

9. A method for treatment of an hypersensitivity reaction associated with atopic dermatitis, comprising administering a composition comprising delipidated and deglycolipidated *Mycobacterium vaccae* cells that have been treated by acid hydrolysis.

10. The method of claim 9, wherein the composition additionally comprises an adjuvant.

11. The method of claim 9, wherein the delipidated and deglycolipidated *Mycobacterium vaccae* cells that have been treated by acid hydrolysis contain galactose in an amount less than 9.7% of total carbohydrate.

12. The method of claim 9, wherein the delipidated and deglycolipidated *Mycobacterium vaccae* cells that have been treated by acid hydrolysis contain glucosamine in an amount greater than 3.7% of total carbohydrate.

* * * * *